United States Patent
Davidson et al.

(10) Patent No.: US 8,952,190 B2
(45) Date of Patent: Feb. 10, 2015

(54) SYNERGISTS

(75) Inventors: Robert Stephen Davidson, Leicester (GB); Shaun Lawrence Herlihy, Chatham (GB)

(73) Assignee: Sun Chemical B.V., Weesp (NL)

( * ) Notice: Subject to any disclaimer, the term of this patent is extended or adjusted under 35 U.S.C. 154(b) by 0 days.

(21) Appl. No.: 13/636,971

(22) PCT Filed: Mar. 25, 2011

(86) PCT No.: PCT/GB2011/000436
§ 371 (c)(1),
(2), (4) Date: Sep. 24, 2012

(87) PCT Pub. No.: WO2011/117591
PCT Pub. Date: Sep. 29, 2011

(65) Prior Publication Data
US 2013/0012611 A1    Jan. 10, 2013

(30) Foreign Application Priority Data
Mar. 25, 2010   (GB) .................................. 1005060.7

(51) Int. Cl.
| C07C 229/00 | (2006.01) |
| C07C 229/18 | (2006.01) |
| C07C 227/10 | (2006.01) |
| C08F 2/48 | (2006.01) |
| C09D 11/101 | (2014.01) |

(52) U.S. Cl.
CPC ............. *C07C 229/18* (2013.01); *C07C 227/10* (2013.01); *C08F 2/48* (2013.01); *C09D 11/101* (2013.01); *C07C 2102/42* (2013.01); *C07C 2103/68* (2013.01)
USPC ............................................. 560/43; 560/50

(58) Field of Classification Search
None
See application file for complete search history.

(56) References Cited

U.S. PATENT DOCUMENTS

2009/0099279 A1    4/2009 Carroy et al.

FOREIGN PATENT DOCUMENTS

| EP | 0474431 A1 | 3/1992 |
| WO | 00/44734 A1 | 8/2000 |

OTHER PUBLICATIONS

Database Caplus Chemical Abstracts Service, Columbus, Ohio, US; Database Accession No. 1960:36619, Abstract of Kaufmann et al., Fette, Seifen, Anstrichmittel.*
D. G. Anderson et al.: Mono and Bis Substituted Amino benzoates as Amine Synergist for UV Curing, Radtech Europe 2005 Conference Exhibition, 2005, XP002656819, RadTech Association, Europe.
International Search Report mailed Dec. 12, 2011 in connection with International Application No. PCT/GB2011/000436.
Written Opinion mailed Dec. 12, 2011 in connection with International Application No. PCT/GB2011/000436.
D.W. Adamson, "Aminoalkyl Tertiary Carbinols and Derived Products. Part I. 3-Amino-1 : 1-diphenylpropan-1-ols", Journal of the Chemical Society, 1949, pp. S144-S155.
Lon J. Mathias et al., "Synthesis of New Hydroxylated Monomers Based on Methacrylate, Dimethacrylate, and Tetramethacrylate Michael Adducts and Photopolymerization Kinetics of Bulk Cross-Linkers", Macromolecules 37:9, May 1, 2004, pp. 3231-3238.
Daniel Sole et al., "Intramolecular Pd(0)-Catalyzed Reactions of [beta]-(2-Iodoanilino) Carboxamides: Enolate Arylation and Nucleophilic Substitution at the Carboxamide Group", The Journal of Organic Chemistry 73:23, Dec. 5, 2008, pp. 9372-9378.
Chinese Office Action issued in counterpart Chinese Application No. 201180015 87.0, dated Jan. 24, 2014. English language translation is also provided.

* cited by examiner

*Primary Examiner* — Karl J Puttlitz
(74) *Attorney, Agent, or Firm* — Charles C. Achkar; Ostrolenk Faber LLP.

(57) ABSTRACT

Compounds of formula (I): wherein Ar represents an, optionally substituted, aryl or heteroaryl group, R represents an, optionally substituted, aryl or heteroaryl group, an optionally substituted straight or branched chain $C_{1-10}$-alkyl, $R^1$ is H or methyl, X is an extender group, n is 0 or an integer between 1 and 12 inclusive, A is a polyol residue wherein the unsubstituted polyol from which the residue is derived has at least y OH groups, and y is an integer>1, can easily be prepared, and are useful as synergists in radiation curing.

(I)

$$\left[ Ar-\underset{R}{N}-CH_2-\underset{R^1}{CH}-\underset{O}{\overset{O}{C}}-O-(X)_n \right]_y - A$$

20 Claims, No Drawings

SYNERGISTS

This application is a National Stage Application of PCT/GB2011/000436, filed Mar. 25, 2011, which claims the benefit of Great Britain Patent Application No. 1005060.7, filed Mar. 25, 2010, both of which are hereby incorporated by reference for all purposes as if fully set forth herein.

The present invention relates to amine synergists and to their use in radiation curing.

Radiation curing is considered to be ecologically friendly technology, and is currently attracting much interest. Of particular importance is the use of ultra-violet, visible and near infra-red radiation to bring about the polymerisation of unsaturated species. By the appropriate choice of unsaturated materials, coatings possessing a remarkable range of properties can be produced. As such, the technology has found use in such diverse applications as: wood and metal coatings; the graphic arts; electronics and optoelectronics; and, production of medical devices and products, to name but a few.

The most frequently used unsaturated compounds are (meth)acrylates i.e. acrylates and methacrylates, since they are fast curing, and many different types are commercially available. In order for light to trigger the polymerisation process, it is necessary for formulations based on (meth)acrylates to contain a material that will absorb light and thereby generate a species which will initiate polymerisation. Such light absorbing compounds are known as photoinitiators. The most frequently used photoinitiators are Type I and Type II.

Type I photoinitiators undergo bond cleavage following the absorption of light to give radicals which attack the double bonds of the polymerisable species, thereby initiating polymerisation. Type II initiators, such as aromatic ketones, are compounds which, following absorption of light, generate radicals, either by hydrogen atom abstraction, or via electron transfer, followed by rapid proton transfer to generate radical species. These photoinitiation processes are well documented in standard texts (c.f. Exploring the Science, Technology and Applications of UV and EB Curing by Stephen Davidson, SITA Technology Ltd., London UK 1999; Photoinitiation Photopolymerization and Photocuring, J-P Fouassier, Hanser Publishers, Munich 1995).

Whilst many compounds can react with the electronically excited Type II photoinitiators to generate radicals, the process is often relatively inefficient. A particular family of compounds capable of reacting efficiently with the excited photoinitiator is the tertiary amines and their derivatives, including amino alcohols and amino acids. Tertiary amines are commonly used and, in the context of radiation curing, are often referred to as amine synergists. The α-aminoalkyl radicals generated as a result of hydrogen abstraction from the tertiary amines are very reactive towards (meth)acrylate double bonds.

Tertiary amines perform yet another useful function in radiation curable systems based on (meth)acrylates, and this is directly related to their mechanism of photo-oxidation [R F Bartholomew and R S Davidson, Journal of the Chemical Society Chemical Communications, (1970), 1174-1175, Journal of the Chemical Society (C) (1971), 2347-2351]. It was found that the α-aminoalkyl radicals produced from tertiary amines react rapidly with oxygen to produce peroxyl radicals. These peroxyl radicals can then attack tertiary amines that have yet to form radicals, thus generating further α-aminoalkyl radicals, i.e. a chain reaction is initiated in which oxygen is sequestered as a peroxidic species.

The UV-curing of formulations based on (meth)acrylates is usually performed in air, which allows the ready ingress of oxygen into the UV-curable formulation. During the photopolymerisation process, the radical intermediates may react with molecular oxygen and be diverted from the polymerisation process, thereby decreasing the efficiency of the cure process. This is known to those skilled in the art as oxygen inhibition. If a suitable tertiary amine, in an appropriate amount, is added to the UV-curable formulation, radicals generated from the amine rapidly scavenge oxygen present in the formulation, thereby allowing the desired polymerisation process to proceed. For this strategy to be successful, the consumption of oxygen within the coating has to proceed, or have the potential to proceed, at a rate that is substantially greater than the rate of ingress of oxygen from the air into the coating.

Tertiary amines commonly used in radiation curing are either aliphatic or aromatic, although hybrid species i.e. compounds containing both aliphatic and aromatic amine moieties, are known. The use of amines in radiation curing has been reviewed [R S Davidson in "Radiation Curing in Polymer Science and Technology" Volume II Polymerisation Mechanisms, eds, J P Fouassier and J F Rabek Elsevier Science Publishers Ltd., Essex, UK (1993)].

Aliphatic amine synergists are frequently used in radiation curable formulations with N-methyldiethanolamine, N,N-dimethylethanolamine and triethanolamine being frequently used. Apart from their high reactivity, these materials possess another advantage, which is that they are optically transparent from ~260 nm up to the near infrared, so that they can be used with photoinitiators which show only a weak absorption above 300 nm. Such photoinitiators include some of the well-established Type I compounds, such as benzil dimethylketal and 2-hydroxy-2-methylpropiophenone, and the ubiquitous Type II photoinitiator benzophenone. Another commercial advantage is their low cost.

A property of the amine synergists which can limit their use is their water solubility. If, during the curing process, the formulation comes into contact with water, as is the case in the photo-litho process, then the amine synergist may be leached from the formulation before the radiation curing process takes place, making the cure ineffective.

There are several other disadvantages to using aliphatic tertiary amines in UV-curable applications, and particularly where packaging for foodstuffs is concerned. These low molecular weight aliphatic amines possess very strong ammoniacal odours which can be readily detected in the cured coating. The use of these amines also leads to marked photo-yellowing of the cured coatings, and is readily seen in overprint varnishes, for example. This yellowing may increase or decrease on exposure to visible light, the extent of each being dependent upon the aspect of the light and the season during which exposure takes place. The colouration and discolouration reactions are reversible and, therefore, the coatings do not exhibit a constant colouration.

An even more serious disadvantage is that the use of these low molecular weight amines leads to the cured coatings containing migratable species. It is well known that migration of species to the surface of the cured films can spoil their aesthetic value, e.g. high gloss. To overcome this problem and that of the odour of the amines, aminoacrylates have been introduced to the market. These materials are derived by reacting secondary amines such as diethylamine or morpholine to (meth)acrylates via the Michael addition reaction. In principle, it is possible to add such an amine to a multifunctional acrylate, such that the final product contains both a tertiary amine and an acrylate group. Such materials are known as polymerisable synergists since, in theory, they can become part of the photopolymer coating (WO 00/44734 to Sartomer Company Inc., "A Compilation of Oligomers and Monomers Commercially Available for UV Today" G Webster, G Bradley, C Lowe, SITA Technology Ltd, 2001, pp 61-69). Such a process has the potential to reduce the percentage of migratable species within the cured coating.

Primary aliphatic amines react with acrylates in the Michael addition reaction, to give products which are formally derived by adding two acrylate groups to one amino group (US 2009/0099279). A disadvantage of using the amino acrylates is that they have to be used at a higher concentration in the UV-curable formulation, in order to be able to attain the level of tertiary amine groups required for good synergistic properties.

Aromatic amine synergists are usually designed so as to possess negligible water solubility. Since these materials usually possess a strong absorption in the 280 to 310 nm region, they are usually used with aromatic ketones which possess strong absorption bands above 300 nm. Materials used with the aromatic amine synergists include thioxanthones, 4-phenylbenzophenone, etc. Frequently used aromatic amine synergists include ethyl 4-N,N-dimethylaminobenzoate, and 2-ethylhexyl 4-N,N-dimethyl aminobenzoate. These amines, like the aliphatic amine synergists, suffer from the disadvantage of contributing to the percentage of migratable species within the UV-cured coating.

Polyalkylene polyol esters of 4-N,N-dimethylaminobenzoic acid have been shown to lead to far fewer migratable species, and this is attributed to the macromolecular polyether chain being a source of α-alkoxy carbon-centred radicals which can participate in the polymerisation process and, hence, tie the synergist into the cross-linked polymer network [D G Anderson, R S Davidson, N Cullum, E Sands, EP-A-822 929, D G Anderson, N R Cullum, R S Davidson, Proceedings RadTech, North America, (1998), 457-467].

The attachment of polymeric tails to synergist and photoinitiators has been described (EP-A-822928) for reducing the percentage of migratable species within a cured coating, but suffers from two major disadvantages. The polymeric moiety might not be of the appropriate type for generating the coating having the desired physical properties and, so, may have a possible deleterious effect on the properties. For example, it is known that introduction of polyethers into formulations can lead to the cured coatings having a poor solvent resistance, decreased hardness and poor weathering properties. Furthermore, the polymeric tail moiety occupies valuable space in the formulation.

The introduction of polymeric chains can have other deleterious effects, such as increasing the viscosity of the formulations, which can only be offset by increasing the percentage of reactive diluent within the formulation. It has also been found that some polymeric chains restrict molecular motion and, in the case of a Type II photoinitiator interacting with a synergist, mobility is of the essence if an efficient bimolecular interaction is to be achieved.

These problems have led to the development of a class of photoinitiator and synergist, known as multifunctional initiators and synergists. These compounds possess a low molecular weight core moiety to which either photoinitiators or amine synergists may be attached. Increasing the number of active components within the molecule leads to an increased chance that the molecule will become covalently bound into the UV-cured coating. Some multifunctional aromatic amine synergists are now available, and all are derivatives of N,N-dimethylaminobenzoic acid.

Two principle routes exist for the manufacture of these materials; either trans-esterification of ethyl 4-N,N-dimethylaminobenzoic acid with branched polyols e.g. pentaerythritol, or transformation of 4-N,N-dimethylaminobenzoic acid into the corresponding acid chloride or anhydride, followed by reaction with a polyol, such as is disclosed in EP-A-1925609 (Agfa Graphics NV), EP-A-1616922 (Agfa Gevaert), EP-A-1765877, US 2003/0073757, WO 03/031502, and US 2007/0004815 (Ashland Chemical Company).

WO 2009/058843 discloses electron donor compounds for use in dental compositions, which are lower alkyl N-methyl-N-phenylaminoacrylates. These compounds are described as having superior colour stability, but only two ethyl esters were prepared, from N-methyl aniline and 4-methyl N-methylaniline.

Whilst many aminoacrylates have been generated using the Michael addition reaction with aliphatic amines as reactants (e.g. WO 00/44734 (Sartomer Company Inc.), EP 1 731 541 (Cytec Industries)), no one has previously reported the generation of aminoacrylates derived from aromatic amines, for use in radiation curing.

Joseph et al., Journal of Molecular Catalysis A: Chemical, 2006, 250(1-2), 210-217, discloses that the addition of primary aromatic amines to acrylates can be carried out using clays as catalysts. Only monoacrylates were used, and the main product is obtained from the 1:1 addition of the amine to the acrylate.

Duan et al., Tetrahedron Letters 2006 47(31), 5433-5436, use a redox-couple (cerium (IV) ammonium nitrate) to effect the addition of the radical cation of the amine to an acrylate.

Nowhere is there described the use of multi-functional acrylates.

WO 2010/029017 discloses an amine-substituted acrylate, designated COINI-3, but there is no disclosure as to how the compound was obtained.

It has now, surprisingly, been found that it is possible to synthesise aromatic amine acrylates in a simple fashion, and that it is possible to obtain new amine synergists that overcome some or all of the problems identified above in relation to the art.

Thus, in a first aspect, the present invention provides a compound of formula (I)

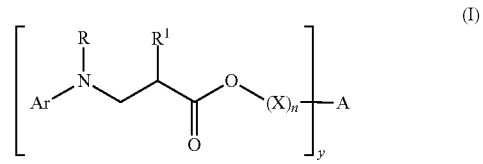

wherein Ar represents an optionally substituted aryl group, R represents an optionally substituted aryl group, or an optionally substituted straight or branched chain $C_{1-10}$-alkyl group, $R^1$ is H or methyl, X is an extender group, n is 0 or an integer between 1 and 12 inclusive, A is a polyol residue wherein the unsubstituted polyol from which the residue is derived has at least y OH groups, and y is an integer >1, with the proviso that, when R=Et, $R^1$=H, X=polyether chain, and A is a glycerol residue, then Ar is not a 4-carboethoxyphenyl group.

There are further provided compounds of formula (Ia), wherein, in the compound of formula (I), the moiety —O—$(X)_n$— is replaced by a moiety —$NR^1$—, wherein each $R^1$ is the same or different.

In an alternative aspect, there is provided the use of a compound of formula (I)

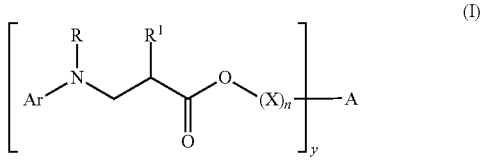
(I)

wherein Ar represents an optionally substituted aryl group, R represents an optionally substituted aryl group, or an optionally substituted straight or branched chain $C_{1-10}$-alkyl group, $R^1$ is H or methyl, X is an extender group, n is 0 or an integer between 1 and 12 inclusive, A is a polyol residue wherein the unsubstituted polyol from which the residue is derived has at least y OH groups, and y is an integer >1, as a synergist in radiation curing.

There is further provided the use of compounds of formula (I), as defined above, as a synergist in the preparation of an article by radiation curing.

Compounds of the invention are useful in all areas where amine synergists are used, and may generally be used in any radiation curing process where a synergist is useful or desired. Examples of industries include the food packaging industry where materials have to be used which show little or no migratability and, as the compounds of the invention are relatively involatile, then they are useful in applications where odour is an issue, such as in the electronics industry, e.g for printed circuit board production.

The compounds of the present invention are particularly advantageous as they are associated with low odour, and produce few, if any, migratable species.

The aryl groups represented by Ar and R may independently be mono- or poly-cyclic, but are preferably mono-, bi-, or tri-cyclic. They may be optionally substituted by at least one substituent selected from: OH; AlkOH, especially methoxy and ethoxy; Alk; phenyl; alkoxycarbonyl; $H_2NCO(O)$-Alk-, especially urethane; HOOC-Alk-; carboxyl; aryl, such as phenyl, fluorenone, benzophenone, and thioxanthone; CO-Alk; arylcarbonyl; —$NAlk_2$; Alk(CO)Ar; Alk(OH)Ar; —$CO_2Alk$, and esters thereof; carboxylic acids or a derivative thereof, such as an ester or an amide; =O; halogen, including fluorine, chlorine, bromine and iodine, especially chlorine and bromine; and CN,
wherein each Alk is individually alkylene or alkyl and is straight or branched chain having 1 to 10 carbon atoms, preferably having from 1 to 6 carbon atoms, inclusive.

In one embodiment, the optional substituent(s) is selected from OH, alkoxy, alkoxycarbonyl, $H_2NCO(O)$-Alk-, especially urethane, HOOC-Alk-, carboxyl, —$NAlk_2$, —$CO_2Alk$, and esters thereof. There is preferably one or zero substituents.

The OH and carboxyl substituents are preferred, as they are easy to manipulate, and precursors for these materials, such as 4-hydroxy N-methylaniline and alkyl N-methylaminobenzoates, are readily available.

Preferred alkyl groups contain 1 to 4 carbon atoms, and more preferably are methyl or ethyl.

Suitable aryl groups include phenyl, naphthalene, anthracene fluorenone, benzophenone, and thioxanthone. Where aryl is a heteroaryl group, it is preferred that no more than three ring members are heteroatoms, more preferably, and particularly that only one member is a heteroatom. Preferred heteroatoms are sulphur and nitrogen, with sulphur being more preferred. In preferred compounds of the invention, each aryl is a monocyclic aryl group, and is preferably substituted or unsubstituted phenyl. Preferred substituents are OH and carboxyl, and derivatives thereof, such as the salts and esters. Salts are not generally preferred.

In general, carboxyl groups are in the form —COOH. Branched alkyl may take the form of singly or multiply branched alkyl, such as t-butyl or 4-methylpentyl, for example. Alkyl groups preferably contain from 1 to 6 carbons, and more preferably from 1 to 4 carbon atoms. Methyl and ethyl are particularly preferred as substituents. Similar considerations apply to hydroxyalkyl groups. Hydroxyalkyl may be substituted by one or more hydroxyl groups, but preferably one. Hydroxycarbonylalkyl typically take the form HOOC-Alk-. Alkylcarbonyl groups take the form Alk-CO—, while alkoxycarbonylalkyl groups take the form AlkOCOAlk-. Alkoxycarbonyl groups take the form AlkOCO—. Any alkyl component preferably has from 1 to 6 carbon atoms, so that alkoxycarbonylalkyl may be hexyl-5-pentanoate or methylmethanoate for example.

Where Ar is monocyclic, substituents may either be in the 2, 3 or 4 position but preferably in the 4 position.

Substituents of choice include alkyl, linear or branched containing up to 10 carbon atoms but preferably from 1 to 6, preferably 1 to 5. Other substituents that may be used include aryl, preferably phenyl, and benzylic groups, alkoxy groups containing an alkyl group of up to 6 carbon atoms, alkyl or dialkylamino groups containing up to 6 carbon atoms, carboxylic acids or a derivative thereof, such as an ester or an amide, =O, cyano, and halogeno groups.

The aryl group may be mono, di or trisubstituted. Preferred is mono-substituted. Monocyclic aryl may be substituted in the ortho, meta or para positions, preferably the para position, when mono-substituted.

Di-substituted aryl groups are preferably ortho and para with the groups being selected from the above.

Tri-substituted aryl groups are preferably di-ortho and para, with the groups being selected from the above.

When R is an alkyl group, this may be straight or branched chain, and contain up to 10 carbons, preferably 1 to 6 carbons, and more preferably 1 to 4. H, methyl and ethyl are preferred meanings of R. When R is a substituted alkyl, then the substituents may suitably be selected from the alkyl substituents given above. The preferred substituents are OH and —$CH_2COOH$, and preferred substituted alkyl groups are $HOCH_2$—, HOEt-, and —$CH_2COOH$.

$R^1$ is H or methyl, and is preferably H.

X may be any group that is used as an extender in the field of polymeric coatings, and as known for initiators and synergists. Suitable extenders may have a formula selected from: —$[O(CHR^2CHR^{2'})_a]_n$—, —$[O(CH_2)_bCO]_n$—, or —$O(CH_2)_bCO]_{n-a}$—$[O(CHR^2CH)]_a$— wherein one of $R^2$ and $R^{2'}$ represents a hydrogen atom and the other represents a hydrogen atom, a methyl group, or an ethyl group, n is as defined, a is an integer from 1 to 2, and b is an integer from 4 to 5. More preferably, X is selected from ethyleneoxy, propyleneoxy, caprolactone and poly(tetrahydrofuran) residues, especially ethoxyl and propoxyl residues.

n is 0 or 1 to 12, preferably 0 or 1 to 6.

y is an integer greater than 1, and may be anything up to about 40. A preferred upper limit is 32. In many preferred compounds, y is 1 to 8, inclusive, and preferably 1 to 6, more preferably 1 to 4, inclusive. In even more preferred compounds y is 2 to 8, inclusive, and preferably 2 to 6, more preferably 2 to 4, inclusive.

The group A may be any suitable residue of a substance, such as illustrated herein, the substance comprising two or more OH groups that can substituted by an acryoyl, preferably acryloyl or methacryloyl, particularly preferably acryloyl. Such polyols are well known in the art, and may be simple alkane polyols, or substances such as tripropylene glycol, pentaerythritol, trimethylolpropane, ditrimethylolpropane, as well as hydroxy terminated polyethers, including ethylene glycol, propylene glycol and butylene glycol, polyesters, polyurethanes, polycarbonates, polycaprolactones, polytetrahydrofurans, and the extended versions of the above. It will be appreciated that, in relation to the compounds of formula (I), the residue A comprises no oxygen atoms which have been substituted by an acryloyl group, these being depicted inside the brackets. For example, if the polyol from which A in the compound of formula (I) is derived is glycerol, and all of the glycerol OH groups are acrylated, then A will be a propyl group substituted at each carbon by the group in square brackets in the compound of formula (I), with y=3.

Suitable residues represented by A typically include $C_{1-10}$ alkyl groups, which may be straight or branched, ethylene glycol and propylene glycol polyethers, ether-linked $C_{1-10}$ alkyl groups, and ring compounds known in the art to confer desirable properties on the cured product, such as tricyclo [$5.2.1.0^{2,6}$]decan-4,8-dimethylene.

Preferred acrylated polyols for use in accordance with the present invention, and upon which the compounds of formula (I) may be based, include; butan-1,4-diol diacrylate, but-2-ene-1,4-diol diacrylate, hexan-1,6-diol diacrylate, triethylene glycol diacrylate, tetraethylene glycol diacrylate, tripropylene glycol diacrylate, tetrapropylene glycol diacrylate, tricyclodecane dimethanol diacrylate, hydroxypivalaldehyde/trimethylolpropane diacrylate, neopentylglycol diacrylate, ethoxylated neopentyl alcohol diacrylate, propoxylated neopentyl alcohol diacrylate, cyclohexan-1,4-dimethanol diacrylate, propoxylated glyceryl triacrylate, trimethylolpropane triacrylate, ethoxylated trimethylolpropane triacrylate, propoxylated trimethylolpropane triacrylate, caprolactone extended trimethylolpropane triacrylate, pentaerythritol triacrylate, pentaerythritol tetraacrylate, tris-(2-hydroxyethyl) isocyanurate triacrylate, pentaerythritol tri and tetraacrylate, ditrimethylolpropane tetraacrylate, dipentaerythritol penta and hexaacrylate, urethane, epoxy, polyester and polycarbonate acrylates.

It is an advantage of the present invention that the compounds described herein are multifunctional aromatic aminoacrylates. These compounds are capable of acting as efficient amine synergists which are of low odour and lead to few, if any, extractable and migratable species in cured coatings derived from (meth)acrylates. The term '(meth)acrylates' is used to indicate both acrylates and methacrylates, and can mean one or the other, as appropriate.

The Michael addition of aromatic amines to acrylates has been previously described (U.S. Pat. No. 6,458,966) in the context of introducing a carboxylic acid function into dyes to aid their linking, via a covalent bond, to biological substrates such as antibodies and enzymes. This process requires the use of an excess of the acrylate component, and the excess acrylate is generally not easy to remove, often requiring chromatography.

Michael addition reactions using extremely harsh experimental conditions, and using cyanides, of aromatic amines are summarised in B D Mather et al., Progress in Polymer Science, (2006) 31, 487-531.

D W Adamson [J. Chem. Soc. (1949), S 144 to S 155) reports the addition of N-methylaniline to ethyl acrylate using 10% acetic acid.

It has now surprisingly been found that it is possible to produce an aminoacrylate without having to use an excess of the acrylate.

Thus, in an alternative aspect, there is provided a process for the preparation of an aminoacrylate, comprising reacting a primary or secondary, preferably aromatic, amine with a (meth)acrylate compound in the presence of an organic, preferably carboxylic, acid. Where the amine is not used in a molar ratio of amine to available acrylate groups in a ratio of ≤1:1, then it is preferred to react any unreacted (meth)acrylate groups with a terminating compound such as illustrated hereinbelow, preferably a secondary amine.

Alternatively, there is provided a process for the preparation of an aminoacrylate, comprising reacting a primary or secondary, preferably aromatic, amine with a (meth)acrylate compound in the presence of an organic, preferably carboxylic, acid, and wherein the molar ratio of amine to available acrylate groups is ≥1:1.

In a further aspect, there is provided a process for the preparation of an aminoacrylate, comprising reacting a primary or secondary, preferably aromatic, amine with a (meth)acrylate compound in the presence of an organic acid, preferably carboxylic, acid, and wherein the ratio of amine to acrylate groups is stoichiometric or in excess.

It is an advantage of the present invention that, by use of an excess of the amine, total conversion of the acrylates can be achieved, with the excess amine being readily removed by steam distillation.

The acid used is preferably in the form of a liquid at the temperature selected for carrying out the reaction, or that the mixture of acid and the reagents is liquid at this temperature. For example, the amine and the acrylate may both be liquid and the acid solid, but wherein the acid is soluble in a mix of the amine and acrylate. It is further preferred that the acid is water soluble in more than sparing amounts. Acids that are liquid at a temperature below 100° C. are preferred. Examples of suitable acids include toluene sulphonic acid, but carboxylic acids are more preferred, such as caproic acid, and glacial acetic acid is more preferred.

The reaction may be conducted at any suitable temperature, from room temperature and pressure up to and including reflux. However, the reaction is generally slow at lower temperatures, and an effective temperature for reaction is generally between 70° C. and 120° C., and more preferably between 80° C. and 100° C. inclusive.

The amount of acrylate groups required is the amount of acrylate groups available for reaction with the amine. Accordingly, polyols bearing several acrylate substituents will be required in proportionally lower molar amounts, in order to keep the amine/acrylate balance, as several amine molecules can react with one polyol bearing multiple acrylate substituents. In the event that the amine is a primary amine, then the acrylates may be present in a ratio of 2:1 to the amine, if it is required that the amine be disubstituted, but a ratio of no more than 1:1 acrylate:amine is generally preferred, and an excess of the amine is most preferred. Where it is desired to obtain an oligomeric compound of the invention, then the proportion of primary amine and multifunctional (meth)acrylate will depend on the nature of the oligomer that it is desired to obtain, and the amount of (meth)acrylate substitution on the polyol residue, and will be readily apparent to the skilled person.

It is possible to use an excess of the amine, and the remainder is typically simple to remove after reaction, by distillation or solvent extraction and phase separation.

The required heating period may be from 6 to 24 hours, and will depend on the reaction. By comparison with secondary amines, primary amines may react with two acrylate groups, but the reaction normally takes longer, and the end product is less efficiently gained. It has been found that primary amines preferably react only with a single acrylate, so that it is possible to stop the reaction at a point where the amine has only reacted with a single (meth)acrylate moiety, such that the remaining position on the amine can provide a useful functional group. In this reaction, a first amount of primary amine can be reacted with a multifunctional (meth)acrylate, the primary amine being in stoichiometric deficit to the (meth) acrylate, and allowing the reaction to go substantially to completion, followed by the addition of further primary amine and reacted such as to react such further primary amine singly with remaining unreacted (meth)acrylate moieties. The amount of the further primary amine will typically be in double, or more, of the required stoichiometric amount, as only 50% of the available positions on the amine groups will be occupied as a result of the second step of the reaction.

The compounds of the present invention typically show a $\lambda_{max}$ at 300 to 304 nm, whereas the main absorption band of 2-ethylhexyl N,N-dimethylaminobenzoate (EHA) extends over the range 300 to 350 nm. It is an advantage of the compounds of the present invention that they enable efficient use of photoinitiators which absorb in the 300 nm region, such as benzophenone, and α-hydroxy acetophenones. It is preferred not to use the compounds of the present invention in the presence of EHA, as EHA acts as an internal light filter.

As noted above, the compounds of the present invention may be obtained by the Michael addition of an aromatic primary or secondary amine to multifunctional (meth)acrylates. Multifunctional (meth)acrylates are well known in the art, and can be prepared from (meth)acrylic acid and di, tri, tetra, penta, and hexafunctional polyols in the presence of suitable catalysts. Multiacryloyl, or acrylated, polyols may also be prepared by esterification of the polyol with either (meth)acryloyl chloride or (meth)acrylic anhydride, for example. Multiacryloyl is used herein to indicate the presence of two or more (meth)acrylate moieties on a vehicle therefor, the vehicle typically being a polyol. As used herein, a polyol is polyhydric compound, having two or more hydroxyl substituents that may be esterified by a (meth)acrylic acid.

In a preferred embodiment, the process of the present invention comprises the use of one or more secondary aromatic amines in a stoichiometric deficit in relation to a multifunctional (meth)acrylated polyol to substitute a proportion of the acrylate moieties by a Michael reaction, and subsequently substituting all or a part of the remaining unsubstituted acrylate groups with a secondary aliphatic amine in a Michael reaction.

When, in a Michael addition, a 1:1 mole ratio of aromatic secondary amine to acrylate is used, the resulting reaction mixture may contain a small amount of unsubstituted acrylate. To ensure that all the acrylate moieties are used, one preferred option is to use an excess of aromatic amine. The excess can be removed by steam distillation. In the above-described alternative, the unused acrylate groups in the reaction mixture are reacted with secondary aliphatic amines via a Michael addition reaction. The products of such reactions yield aliphatic aminoacrylates which are known to have good synergistic properties, c.f. WO 00/44734 (Sartomer), which discloses the use of morpholine for this purpose. WO 2009/030658 discloses the addition of diethylamine.

It has surprisingly been found that the resulting, mixed aromatic-aliphatic amino acrylates are synergistic, and frequently strongly synergistic. In particular, it is preferred to use a deficit of aromatic amine in a ratio of 0.6 to 0.9 moles amine to 1.0 mole equivalent of the acrylate. Such products show enhance curing properties. Preferred secondary aliphatic amines include, but are not limited to, morpholine and N-methyl ethanolamine. The enhancement in synergistic action is surprising, especially as there is no reason to expect that aliphatic aminoacrylates are more reactive than aromatic aminoacrylates.

Without being limited by theory, it appears that the alkyl parts and aryl parts of such synergists are themselves acting synergistically. Amine synergists generally act in two ways: helping to reduce oxygen inhibition and being a source of radicals which initiate polymerisation. The extent to which these processes contribute to the amines ultimate performance has never been determined, but it is known that aliphatic amines are photo-oxidised more rapidly than aromatic amines, and it is likely that, in these hybrid materials, the aliphatic amine enhances oxygen inhibition, while the aromatic amine promotes the radical reaction. In addition, aromatic amino acrylates have only now been made available as provided by the process of the invention. Accordingly, the present invention further provides an aromatic aminoacrylate, preferably as described herein.

The process of the present invention provides a way of making mixed aromatic-aliphatic amino acrylates in an environmentally friendly fashion, which is substantially waste-free. This process further provides means to obtain compounds containing aliphatic amino-acrylates having limited water-solubility.

Compounds of the invention are illustrated in the following formulae (2) to (4), wherein the substituents are as defined above, and if any substituent occurs more than once, then each occurrence may be the same or different. The sum of y+a is equal to no more than the number of OH groups on the equivalent unsubstituted polyol group represented by A.

Compounds having formula (2) may be derived by adding a secondary aromatic amine to a (meth)acrylate.

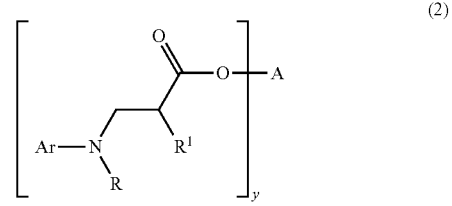

(2)

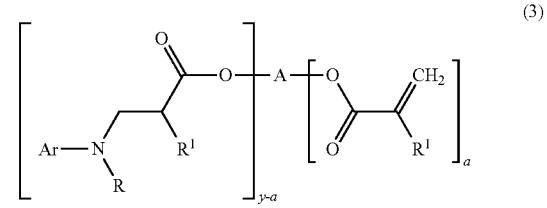

(3)

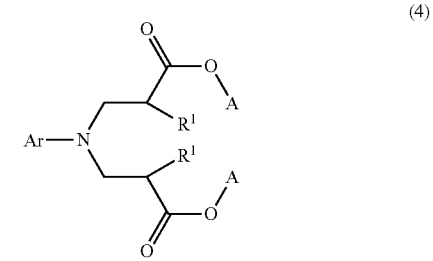

(4)

Compounds of the formula (3), may be derived by the Michael addition of the secondary aromatic amine to a (meth) acrylate. Such materials are known as polymerisable aromatic amine synergists.

Compounds of the formula (4) may be derived by the addition of a primary aromatic amine to a (meth)acrylate, using a two step reaction involving the addition of one molecule of the acrylate to one molecule of the amine, followed by reaction of this product with a further molecule of the acrylate. If desired, an unreacted (meth)acrylate residue may be left at the terminus of the polyol A, to provide an aromatic amine synergist.

It will be appreciated that the compounds of formula (4) can form oligomers and polymers where the (meth)acrylate is multifunctional. For the avoidance of doubt, where the term 'acrylate' is used herein, this includes reference to the corresponding methacrylate, unless otherwise apparent from the context. The term 'multifunctional', in relation to a (meth)acrylate compound, includes any acrylate having more than one acrylate group. Suitable examples are provided elsewhere herein.

In order to control the amount of oligomerisation, it is preferred to use a restricted amount of primary amine, such that there is a stoichiometric deficit of the primary amine compared to the multifunctional acrylate. The deficit may then be made up by the addition of a secondary amine, such as morpholine or N-methyl aniline. The secondary amine may be added together with, before, or after the primary amine, but it is generally preferred to react the primary amine to completion, or substantially near to completion, and then to add the secondary amine. The amount of secondary amine added may be in deficit in order to leave functional groups that may be further derivatised, for example, may be added to substantially correspond to the deficit from the primary amine, or may be added in excess, with any excess optionally being subsequently removed.

This type of reaction may be used to prepare chains of multifunctional acrylates. An example is as follows. Hexane-1,6-diol diacrylate is reacted with aniline to give the following reaction, in which $A = -(CH_2)_6-$, the polyol residue being a residue of hexane diol.

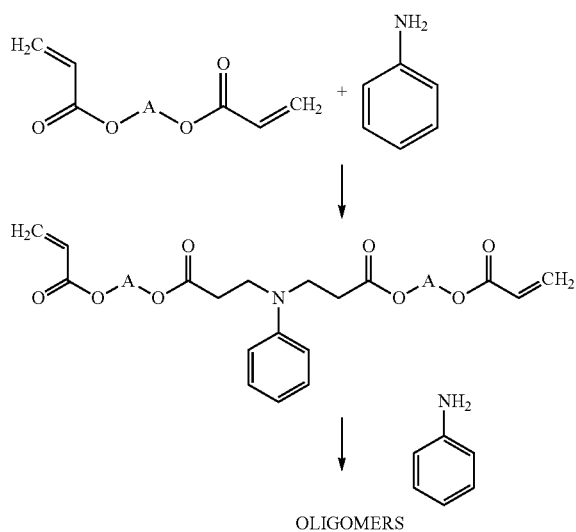

OLIGOMERS

As noted above, the oligomers generated in this fashion possess terminal acrylate groups which may be further reacted with either secondary aromatic or aliphatic amines, for example.

Oligomers of the present invention provide preferred embodiments. These oligomers generally provide enhanced cure rate. In the ink test described in the accompanying Examples, between 10% and 30% less passes were required for curing, compared to non-oligomeric compounds of the invention.

Thus, in a preferred embodiment, there is provided a compound of formula (4)

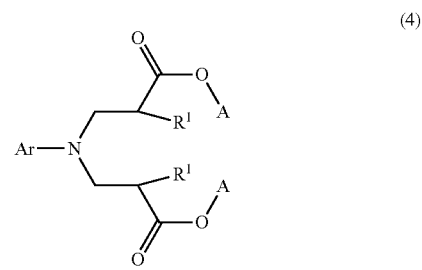

(4)

in the form of an oligomer. In such oligomers, the polyol residue A is substituted by two or more (meth)acrylate groups, and wherein (meth)acrylate groups on different polyol residues are linked, or bridged, by a group >N—Ar, or terminated, preferably by a group —NR(Ar), wherein R and Ar are as defined, and wherein at least three polyol residues are so linked.

Preferred multifunctional acrylates have 2 to 6 (meth)acrylate moieties.

The (meth)acrylate terminal groups may be terminated with primary amines as described above, or by secondary aromatic or aliphatic amines, thiols, phosphines, or materials containing acidic C—H bonds, especially heteroaryl groups Amines are preferred, especially secondary aliphatic and aromatic amines with the aromatic amines being particularly preferred.

The oligomers of the invention generally have enhanced reactivity. One group of preferred oligomeric synergists contains aliphatic amines, and has low hydrophilicity, volatility and odour.

The terminal acrylate groups of the oligomers of the invention may be left unmodified. Such oligomers may be used as amino-acrylate synergists, and may also serve as polymerisable oligomeric aromatic amine synergists.

In one embodiment wherein the polyol is diol, the compounds may be represented by the formula:

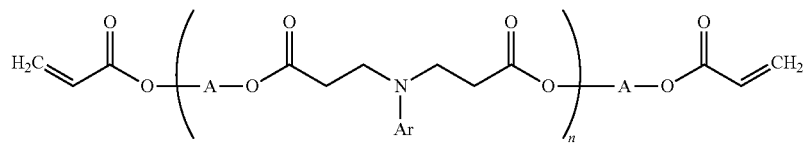

in which A, n and Ar are as defined.

It will be appreciated that the greater the proportion of primary amine used in the manufacture of the oligomers of the present invention, the more gel-like and, ultimately, solid, the resulting product will be.

In one preferred embodiment, trimethylolpropane tetraacrylate is oligomerised with aniline and terminated with N-methyl aniline. At low levels, the aniline may be used to increase the molecular weight, by oligomerisation, of the product, for example.

The addition product of an aromatic primary or secondary amine, such as N-methylaniline, and acrylic acid can be used to esterify a range of polyols, thereby providing an alternative process of obtaining the compounds of the present invention. This is useful where such products may not otherwise be available by reaction of the amine with acrylate esters. It has also been established that N,N-dimethylacrylamide can function as a Michael acceptor, thereby demonstrating that the process of the present invention may be used to obtain the compounds of formula (Ia).

These oligomers of the present invention have been found to be effective amine synergists having the advantage that they are non-odorous and are efficiently incorporated into the cross-linked poly(meth)acrylate structure following UV or EB curing. These properties are maintained when the aromatic amino acrylate contains free (meth)acrylate groups.

End users will choose a particular synergist based on its cure properties, viscosity, and its effect upon the physical properties of the cured coating.

Prior to curing, formulations based on the amine synergists of the present invention can be applied to a surface by any of the commonly used processes, including; spray, roller, dip, and pad coating techniques. Formulations may be applied to substrates such as wood, metal, paper, plastic, glass, fabric, fibre ceramics, concrete, plaster etc. The formulations can be cured using standard UV-curing lamps e.g. medium and high pressure mercury lamps, xenon and xenon/mercury lamps, LED and excimer lamps, provided that the formulations contain an appropriate photoinitiator.

The compounds of the present invention may be used with any free radical producing photoinitiators known in the art, such as those listed in "A Compilation Of Photoinitiators Commercially Available For UV Today", K Dietliker SITA Technology Ltd, Edinburgh, London UK 2002. In addition, many of the compounds of the present invention, having low nucleophilicity, may be used in cationic curing systems where they behave as sensitisers.

Aspects and embodiments of the present invention include:

a. A compound of formula (I):

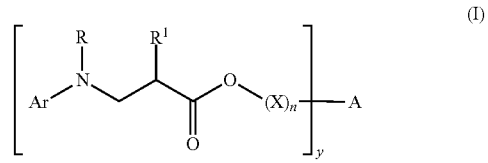

wherein Ar represents an optionally substituted aryl group, R represents an optionally substituted aryl group, or an optionally substituted straight or branched chain $C_{1-10}$-alkyl group, $R^1$ is H or methyl, X is an extender group, n is 0 or an integer between 1 and 12 inclusive, A is a polyol residue wherein the unsubstituted polyol from which the residue is derived has at least y OH groups, and y is an integer >1.

b. Compounds of formula (I) in which any alkyl group contains 1 to 4 carbon atoms, and are preferably methyl or ethyl.

c. Compounds of formula (I) in which any aryl is optionally substituted and is a monocyclic aryl group, and is preferably phenyl.

d. Compounds of formula (I) comprising at least one substituted aryl, wherein the substituent or substituents are individually selected from the group consisting of: OH, alkoxy, alkoxycarbonyl, $H_2NCO(O)$-Alk, especially urethane, HOOC-Alk, carboxyl, and esters thereof, wherein Alk is straight or branched chain alkyl having from 1 to 6 carbon atoms, inclusive.

e. Compounds of formula (I) in which Ar is monocyclic aryl, optionally substituted in the 4 position.

f. Compounds of formula (I) in which R is H, methyl or ethyl.

g. Compounds of formula (I) in which $R^1$ is H.

h. Compounds of formula (I) in which X has a formula selected from: $-[O(CHR^2CHR^{2\prime})_a]_n-$, $-[O(CH_2)_b CO]_n-$, or $-O(CH_2)_bCO]_{n-a}-[O(CHR^2CH)_a-$ wherein one of $R^2$ and $R^{2\prime}$ represents a hydrogen atom and the other represents a hydrogen atom, a methyl group, or an ethyl group, n is as defined, a is an integer from 1 to 2, and b is an integer from 4 to 5. X is preferably selected from ethyleneoxy, propyleneoxy, caprolactone and poly(tetrahydrofuran) residues, especially ethoxyl and propoxyl residues.

i. Compounds of formula (I) in which n is 0 or 1 to 12, preferably 0 or 1 to 6.

j. Compounds of formula (I) in which A is selected from tripropylene glycol, pentaerythritol, trimethylolpropane, ditrimethylolpropane, as well as hydroxy terminated polyethers, polyesters, polyurethanes, polycarbonates, polycaprolactones, polytetrahydrofurans, and the extended versions thereof.

k. A process for the preparation of an aminoacrylate, comprising reacting a primary or secondary, preferably aromatic, amine with a (meth)acrylate compound in the presence of an organic, preferably carboxylic, acid, and wherein the molar ratio of amine to available acrylate groups is ≥1:1.

l. A process for the preparation of an aminoacrylate, comprising reacting a primary or secondary, preferably aromatic, amine with a (meth)acrylate compound in the presence of an organic acid, preferably carboxylic, acid, and wherein the ratio of amine to acrylate groups is stoichiometric or in excess.

m. A process as above, wherein the amine is present in excess.

n. A process as above, wherein the acid is a liquid at the reaction temperature.

o. A process as above, wherein the acid is water soluble in more than sparing amounts.

p. A process as above, wherein the acid is a carboxylic acid, and is preferably glacial acetic acid.

q. A process as above, wherein the ratio of acrylate:amine is no more than 1:1.

r. A process as above, wherein the (meth)acrylate is selected from; butan-1,4-diol diacrylate, but-2-ene-1,4-diol diacrylate, hexan-1,6-diol diacrylate, triethylene glycol diacrylate, tetraethylene glycol diacrylate, tripropylene glycol diacrylate, tetrapropylene glycol diacrylate, tricyclodecane dimethanol diacrylate, hydroxypivalaldehyde/trimethylolpropane diacrylate, neopentylglycol diacrylate, ethoxylated neopentyl alcohol diacrylate, propoxylated neopentyl alcohol diacrylate, cyclohexan-1,4-dimethanol diacrylate, propoxylated glyceryl triacrylate, trimethylolpropane triacrylate, ethoxylated trimethylolpropane triacrylate, propoxylated trimethylolpropane triacrylate, caprolactone extended trimethylolpropane triacrylate, pentaerythritol triacrylate, pentaerythritol tetraacrylate, tris-(2-hydroxyethyl)isocyanurate triacrylate, pentaerythritol tri and tetraacrylate, ditrimethylolpropane tetraacrylate, dipentaerythritol penta and hexaacrylate, urethane, epoxy, polyester and polycarbonate acrylates.

Materials
Propoxylated glycerol triacrylate OTA 480 Cytec Industries;
Ethoxylated trimethylolpropane triacrylate Cytec Industries IRR 560;
Ethoxylated pentaerythritol tetra acrylate Sartomer SR 494;
Iso bornyl acrylate Sartomer SR 506;
Trimethylolpropane triacrylate Sartomer SR 351;
Hexane-1,6-diol diacrylate Sartomer SR 238
Penta erythritol tetra acrylate Sartomer SR 295
Di-trimethylolpropane tetra acrylate Sartomer SR 351
Ethoxylated neo-pentyl glycol diacrylate Photomer 4160 (Cognis)
Di pentaerythritol hexa acrylate Sartomer SR 399
Tripropylene glycol diacrylate Sartomer SR306
2-ethylhexyl N,N-dimethylaminobenzoate (Genocure™ EHA) from Rahn AG
Tricyclo[5.2.1.02,6]decan-4,8-dimethanol diacrylate Polymer Technologies Eterna EM 2204.
Ethoxylated neo-pentyl glycol diacrylate
2-Isopropylthioxanthone, IGM resins Omnirad ITX
Poly(ethylene glycol) diacrylate ($M_n$~258), Sigma-Aldrich
n-hexyl acrylate, Sigma-Aldrich
Ethyl 4-aminobenzoate Lambson Fine Chemicals,
N,N-dimethylacrylamide, Sigma-Aldrich
Acrylic acid Sigma-Aldrich,
Poly(ethylene glycol) diacrylate ($M_n$~258) Sigma-Aldrich
N-ethylaniline, Sigma-Aldrich
Sodium cyanoborohydride Sigma-Aldrich,
Aqueous formaldehyde (37%) Sigma-Aldrich,
Dimethyl sulfate Sigma-Aldrich
Ethyl di-isopropylamine Sigma-Aldrich

EXAMPLES

Example 1

Michael addition of N-methylaniline to ethyl acrylate

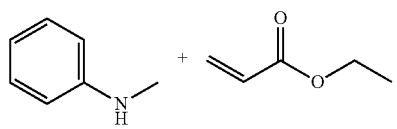

N-methylaniline (5.35 g) was added to glacial acetic acid (15 ml) containing 25 g ethyl acrylate (5× excess) and the mixture heated under reflux for 5 hr. The acetic acid was removed by distillation under reduced pressure and the excess ethyl acrylate separated from the product via distillation in vacuo using a Kugelrohr distillation apparatus.

The product, ethyl 3-(N-methyl-N-phenylamino)propanoate,

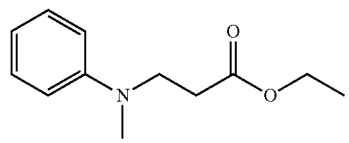

is a lightly coloured low viscosity yellow oil. An IR spectrum showed absorptions characteristic of an ester group (1730 cm$^{-1}$) and the C—N stretch of an aromatic amine (1600 cm$^{-1}$).

$^1$H NMR δ 1.2 (CH$_3$—CH$_2$ 3H t), 2.55 (CH$_2$—CO, 2H t), 2.9 (CH$_3$—N s), 3.65 (CH$_2$—N), 4.1 (CH$_2$—CH$_3$, 2H q).

This Example demonstrates that the technique disclosed in U.S. Pat. No. 6,458,966 can be adapted to enable the preparation of multifunctional amine synergists.

Example 2

Michael addition of N-methylaniline to isobornyl acrylate

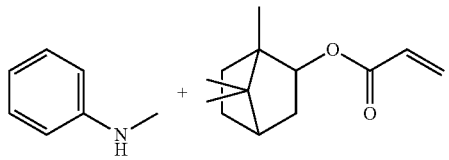

Synthesis of exo-(1R)-1,7,7-trimethylbicyclo[2,2,1]heptan-2-ol 3-(N-methyl-N-phenylamino)propionate

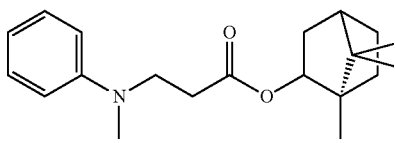 [SMILES: CN(CCC(=O)OC1CC2CC[C@]1(C)C2(C)C)c1ccccc1]

N-Methylaniline (5.35 g) was added to glacial acetic acid (20 ml) containing iso-bornyl acrylate (30.8 g excess) and the mixture heated under reflux for 6 hrs. The cooled reaction mixture was poured into water (150 ml) and then extracted with dichloromethane (30 ml)[extract 1]. The dichloromethane layer [extract 1] was further washed with 2M hydrochloric acid (80 ml). Neutralisation of the acid layer with sodium hydroxide (5 g) was followed by extraction with dichloromethane (40 ml) [extract 2]. The dichloromethane layer [extract 2] was dried over anhydrous potassium carbonate and the solvent removed by evaporation to give a small residue identified by infrared spectroscopy as N-methylaniline. The dichloromethane from the extract was removed by distillation to give an oil, the infrared spectrum of which showed no trace of N-methyl aniline. The unreacted isobornyl acrylate was separated from the product via distillation in vacuo (1 mbar) using a Kugelrohr apparatus. The product was a yellow-coloured oil having an infrared spectrum which did not show any noticeable absorptions due to an acrylate group but did show strong absorptions typical of an ester and an aromatic amine—1730 cm$^{-1}$ (ester carbonyl), 1600 cm$^{-1}$ (C—N stretch).

$^1$H NMR (CDCl$_3$) δ 0.8 and 0.9 (CH$_3$ of isobornyl group)

Example 3

Michael addition of N-methylaniline to iso-bornyl acrylate in which the excess of the acrylate is reduced Synthesis of exo-(1R)-1,7,7-trimethylbicyclo[2,2,1]heptan-2-ol 3-(N-methyl-N-phenylamino)propionate (formulae as for Example 2).

A reaction mixture composed of N-methylaniline (5.35 g) iso-bornyl acrylate (15.4 g) and glacial acetic acid (15 ml) was heated under reflux for 6 hr and the excess acid. Removal of the acetic acid by distillation in vacuo gave a residue the infrared spectrum of which showed no sign of the presence of N-methyl aniline, demonstrating that the use of excess acrylate in these reactions is not necessary.

IR (thin film). Strong absorptions due to the ester group (1740 cm$^{-1}$) and aromatic amine (1600 cm$^{-1}$) were present.

$^1$H NMR (CDCl$_3$) δ 0.8 and 0.9 (CH$_3$ of isobornyl group), 2.5 (CH$_2$—CO, 2H t), 2.9 (CH$_3$—N, 3H s), 3.6 (CH$_2$—N, 2H, t), 6.7 (aromatic C—H 3H m), 7.2 (aromatic C—H, 2H m).

Example 3 demonstrates that it is not necessary to use an excess of the acrylate.

Example 4

Reaction of N-methylaniline with a multifunctional acrylate (trimethylolpropane triacrylate, Sartomer 351)

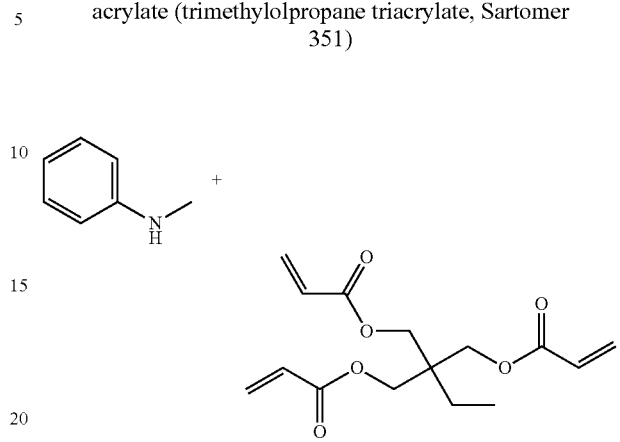

Synthesis of 1,1,1-trimethylolpropane tri-(3-[N-methyl-N-phenylamino]propionate)

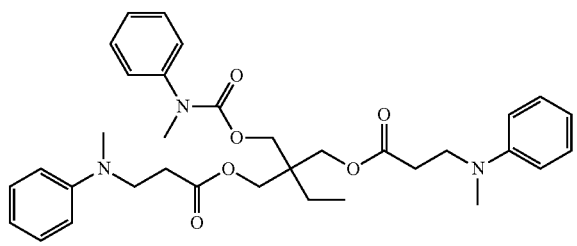 [SMILES: CCC(COC(=O)CCN(C)c1ccccc1)(COC(=O)CCN(C)c1ccccc1)COC(=O)N(C)c1ccccc1]

N-methylaniline (14.81 g) was added to glacial acetic acid (25 ml) containing trimethylolpropane triacrylate (16.05 g) and the mixture heated under reflux for 12 hr. The acetic acid was removed by distillation in vacuo to give a viscous oil. An infrared spectrum of the product showed that very few acrylate residues were present. Strong absorptions due to an ester and an aromatic amine group were present (1740 and 1600 cm$^{-1}$).

$^1$H NMR δ 0.9 (CH$_3$, 3H, t), 1.4 (CH$_2$, 2H, q), 2.5 (CH$_2$—CO, 6H t), 2.9 (CH$_3$—N, 9H s), 3.6 (CH$_2$—N, 6H, t), 4.0 (CH$_2$—O, 6H, s), 6.7 (aromatic C—H 9H m), 7.2 (aromatic C—H, 6H m).

Example 5

Reaction of aniline with isobornyl acrylate

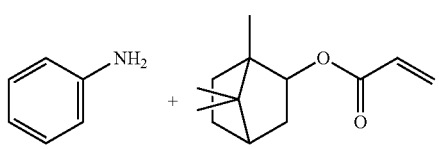

Expected synthesis of (i) exo-(1R)-1,7,7-trimethylbicyclo[2,2,1]heptan-2-ol 3-(N-phenylamino)propionate

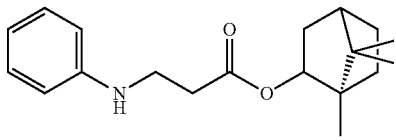 [SMILES: CC1(C)C2CC[C@@]1(C)C(OC(=O)CCNc1ccccc1)C2]

and (ii) bis((1R)-1,7,7-trimethylbicyclo[2.2.1]heptan-2-yl) 3,3'-(phenylazanediyl)dipropanoate

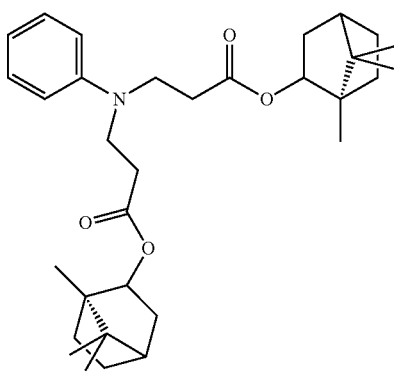 [SMILES: CC1(C)C2CC[C@@]1(C)C(OC(=O)CCN(CCC(=O)OC1CC3CC[C@]1(C)C3(C)C)c1ccccc1)C2]

In these reactions attempts were made to react 1 mole of the amine with 2 moles of the acrylate.

Aniline (2.32 g) was added to glacial acetic acid (15 ml) containing isobornyl acrylate (10.4 g) and the mixture heated under reflux for 6 hr. Following removal of the acetic acid by distillation in vacuo a residue remained an infrared spectrum of which showed the presence of both acrylate and N—H groups, i.e. the reaction appears not to have gone to completion and the compound of formula (i) above obtained.

A reaction having the same composition as above was heated under reflux for 17 hr. The acetic acid was removed by distillation in vacuo to give an oily residue an infrared spectrum of which showed that very little acrylate remained unreacted, indicating that the compound of formula (ii) above was obtained. Strong absorptions due to the ester group (1730 cm$^{-1}$) and aromatic amine (1600 cm$^{-1}$) were present.

This Example demonstrates that it is possible to use a primary aromatic amine to react with two acrylate moieties.

Example 6

Use of the Aromatic Aminoacrylates as a Synergist

A formulation containing an aromatic epoxy acrylate resin (Actilane 320 F, 42.05), reactive diluent tripropylene glycol diacrylate (42.05 g) and photoinitiator iso-propylthioxanthone (2.52 g) was prepared. To one portion of the formulation (20 gm) was added the amine synergist ethyl 4-N,N-dimethylaminobenzoate (1.25 gm) and to another portion (20 gm) was added amine synergist ethyl 3-(N-methyl-N-phenyl) propionic acid (1.25 g), as obtained in Example 1 above, was added. After thorough mixing of the formulations, a little of each formulation was spread on a glass microscope slide and then another microscope slide applied to the film so as to produce a sandwich of the formulation. The formulations were exposed to black light bulbs housed in a thin-layer-chromatography lamp unit. After 3 seconds both formulations had cured as evidenced by the fact that the sandwiches could not be broken apart i.e. a glass laminate had been produced.

This Example demonstrates that compounds prepared by a process of the invention are capable of performing as synergists.

Example 7

Reaction of N-methylaniline with hexan-1,6-diol diacrylate

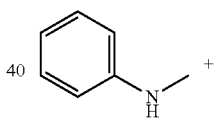

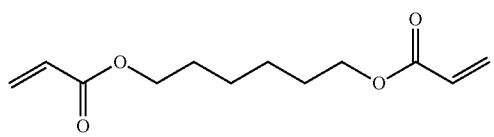

Synthesis of hexane-1,6-diol di-(3-[N-methyl-N-phenylamino]propionate)

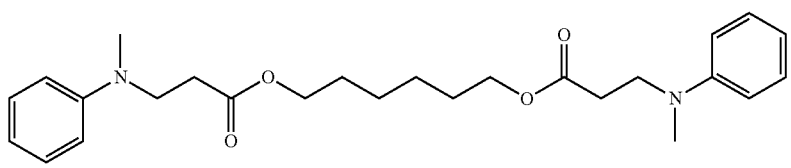 [SMILES: CN(CCC(=O)OCCCCCCOC(=O)CCN(C)c1ccccc1)c1ccccc1]

N-methylaniline (6.43 g 0.06 moles) was added to hexan-1,6-diol diacrylate (4.52 g, 0.02 moles) in glacial acetic acid (10 ml). The mixture was heated at 100° C. for 2 hours. The glacial acetic acid was removed by vacuum distillation and the residue submitted to steam distillation to remove the unreacted N-methylaniline. The residue from the steam distillation was extracted with toluene (30 ml). The toluene layer was washed twice with water (40 ml) and then dried over anhydrous magnesium sulphate. Following filtration to remove the magnesium sulphate, the toluene was removed by vacuum distillation to leave a light-brown coloured oil (7.95 g). An infra red spectrum showed that the acrylate had been totally consumed during reaction and that the steam distillation had been effective in removing unreacted methylaniline. The IR spectrum also showed absorptions typical of a saturated ester (1723 cm$^{-1}$) and the C—N stretch of an aromatic amine (1600 cm$^{-1}$). $^1$H NMR δ 1.2 (CH$_2$ 4H t), 1.4 (CH$_2$, 4H, t), 2.5 (CH$_2$—CO, 4H t), 2.9 (CH$_3$—N, 6H s), 3.6 (CH$_2$—N, 4H, t), 4.0 (CH$_2$—O, 4H, s), 6.7 (aromatic C—H 6H m), 7.2 (aromatic C—H, 4H m).

This Example illustrates the reaction of a difunctional acrylate.

The same procedure as for Example 7 above was adopted, but using 2-hydroxyeththyl acrylate (5.8 g) and N-methylaniline (5.35 g) and glacial acetic acid (15 ml). An infra red spectrum showed the presence of hydrogen bonded hydroxyl groups) 3300 to 3600 cm$^{-1}$, saturated ester at 1723 cm$^{-1}$, and the C—N stretch of an aromatic amine at 1600 cm$^{-1}$. $^1$H NMR, 2.5 (CH$_2$—CO, 2H t), 2.9 (CH$_3$—N, 3H s), 3.6 (CH$_2$—N, 2H, t), 4.2 (CH$_2$—O, 4H, s), 6.7 (aromatic C—H 3H m), 7.2 (aromatic C—H, 2H m).

This Example demonstrates that a monofunctional acrylate which is functionalised can be used. The presence of a Example 9

Reaction of N-methylaniline with tripropylene glycol diacrylate

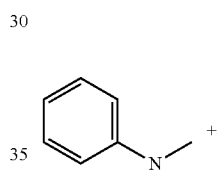

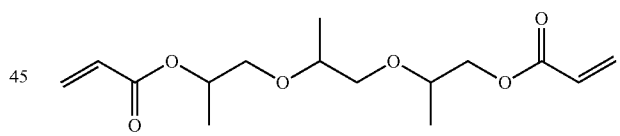

Example 8

Reaction of 2-hydroxyethyl acrylate with N-methylaniline

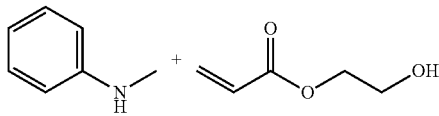

Synthesis of 2-hydroxyethyl 3-(N-methyl-N-phenylamino)propionate

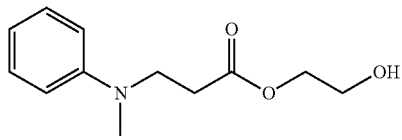 [SMILES: CN(CCC(=O)OCCO)c1ccccc1]

Synthesis of tripropylene glycol di-(3-[N-methyl-N-phenylamino]propionate)

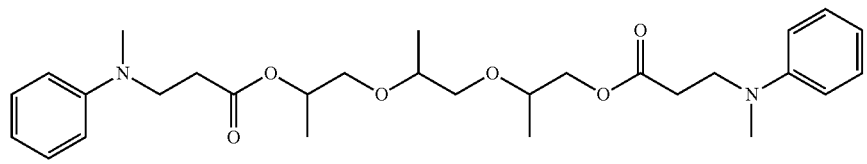 [SMILES: CC(COC(=O)CCN(C)c1ccccc1)OCC(C)OCC(C)OC(=O)CCN(C)c1ccccc1]

N-methylaniline (6.50 g 0.061 moles) was added to tripropyleneglycol diacrylate (6.0 g, 0.02 moles) in glacial acetic acid (10 ml). The mixture was heated at 100° C. for 2 hours. The glacial acetic acid was removed by vacuum distillation and the residue submitted to steam distillation to remove the unreacted N-methylaniline. The residue from the steam distillation was extracted with toluene (30 ml). The toluene layer was washed twice with water (40 ml) and then dried over anhydrous magnesium sulphate. Following filtration to remove the magnesium sulphate, the toluene was removed by vacuum distillation to leave a light-brown coloured oil (10.01 g). An infra red spectrum showed that the acrylate had been totally consumed during reaction and that the steam distillation had been effective in removing unreacted methylaniline. The product showed strong absorptions in its IR spectrum due to the ester group (1740 cm$^{-1}$) and aromatic amine (1600 cm$^{-1}$). $^1$H NMR, 1.1 (CH$_3$, 9H, m) 2.6 (CH$_2$—CO, 4H t), 2.9 (CH$_3$—N, 6H s), 3.4 (CH$_2$—O, 4H m), 3.6 (CH$_2$—N, 4H, t), 4.2 (CH$_2$—O, 6H, m), 5.0 (CH—O, 3H m), 6.7 (aromatic C—H 6H m), 7.2 (aromatic C—H, 4H m).

This Example, in common with Example 7, illustrates the reaction of a difunctional acrylate.

Unreacted N-methylaniline remains, since this was used in excess. The amount of aniline used was based on an equivalent molar amount of neopentyl glycol diacrylate. However, since the material used is ethoxylated, then the percentage of acrylate groups in the material is reduced. The glacial acetic acid was removed by vacuum distillation and the residue subjected to steam distillation to remove the unreacted N-methylaniline. The residue from the steam distillation was extracted with toluene (30 ml). The toluene layer was washed twice with water (40 ml) and then dried over anhydrous magnesium sulphate. Following filtration to remove the magnesium sulphate, the toluene was removed by vacuum distillation to leave a light-brown coloured oil (7.28 g). An infra red spectrum showed that the acrylate had been totally consumed during reaction and that the steam distillation had been effective in removing unreacted methylaniline. Absorptions associated with a saturated ester (1725 cm$^{-1}$) and an aromatic amine (1600 cm$^{-1}$) were also observed.

This Example shows the use of a second generation difunctional acrylate, in which the diol has been elaborated by reaction with ethylene oxide prior to acrylation.

Example 10

Reaction of ethoxylated neopentylglycol diacrylate with N-methylaniline

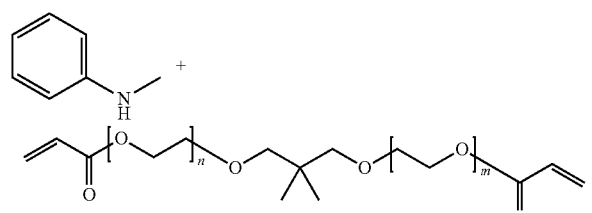

Synthesis of ethoxylated 2,2-dimethylpropane-1,3-diol di-(3-[N-methyl-N-phenylamino]propionate)

Example 11

Reaction of tricyclo[5.2.1.0$^{2,6}$]decan-4,8-dimethanol diacrylate with N-methylaniline

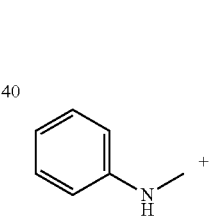

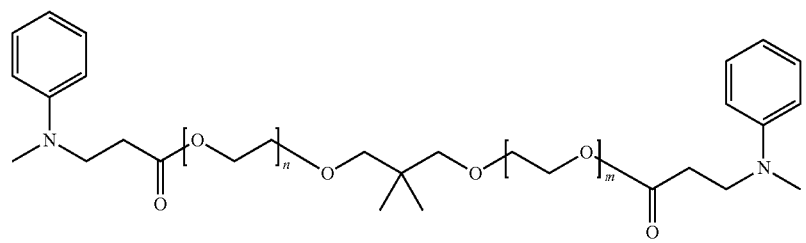

The extent of ethoxylation is not absolute and is represented by n and m in the above formulae. In this and following Examples, n, m, p, and q are all used to indicate multipliers for ethoxylation and propoxylation, and individually are integers between one and six, inclusive.

N-methylaniline (5.0 g 0.061 moles) was added to ethoxylated neopentyl glycol diacrylate (4.24 g) in glacial acetic acid (10 ml). The mixture was heated at 100° C. for 2 hours.

-continued

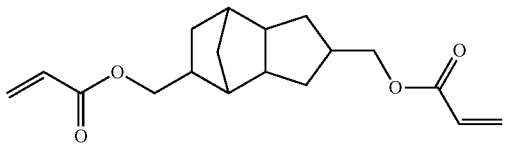

Synthesis of tricyclo[5.2.1.0$^{2,6}$]decan-4,8-dimethanol di-(3-[N-methyl-N-phenylamino]propionate)

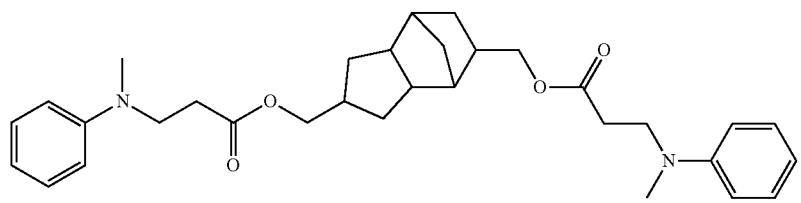 [SMILES: CN(CCC(=O)OCC1CC2C3CC(COC(=O)CCN(C)c4ccccc4)C(C3)C2C1)c1ccccc1]

Reaction conditions similar to those of Example 4 were used, but employing a racemic mixture of the diacrylate (6.04 g), N-methylaniline (4.3 g) and glacial acetic acid (10 ml).

Following removal of the acetic acid, an oil remained which showed strong absorptions in its IR spectrum due to the ester group (1735 cm$^{-1}$) and aromatic amine (1600 cm$^{-1}$).

$^1$H NMR, δ 2.5 ($CH_2$—CO, 4H t), 2.9 ($CH_3$—N, 6H s), 3.6 ($CH_2$—N, 4H, t), 4.2 ($CH_2$—O, 4H, s), 6.7 (aromatic C—H 6H m), 7.2 (aromatic C—H, 4H m).

This Example illustrates the reaction of a diacrylate whose structure imparts hardness to a coating. The resulting compounds are useful for producing hard, scratch resistant coatings.

Example 12

Reaction of ethyl 4-aminobenzoate with n-hexyl acrylate

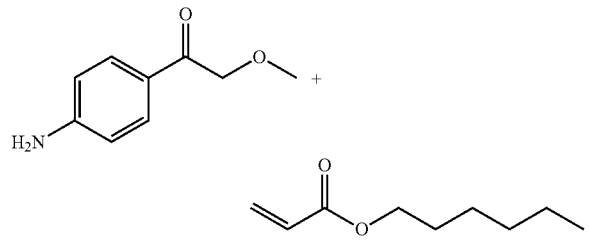

Synthesis of n-hexanol 3-(N-[ethyl 4-carboxyphenylamino])propionate

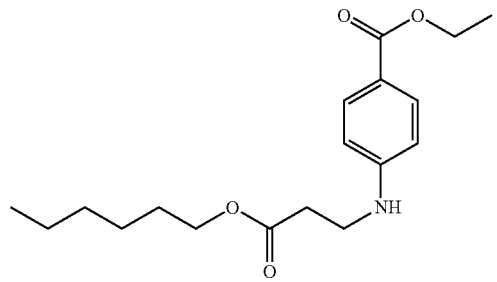 [SMILES: CCCCCCOC(=O)CCNc1ccc(C(=O)OCC)cc1]

Ethyl 4-aminobenzoate (4.12 g, 0.025 mole) was added to n-hexyl acrylate (8.1 g 0.052 mole) in glacial acetic acid (10 ml), and the mixture heated with stirring for 2 hours at 100° C. The acid was removed via vacuum distillation to leave a brown-coloured oil. The oil was distilled in vacuo at 0.1 mm of mercury. Unreacted n-hexyl acrylate was collected up to 120° C. At 220° C. an oil distilled which subsequently solidified on cooling. An IR (mull) showed the presence of N—H bonds at 3320 and 3380 cm$^{-1}$, two ester carbonyls at 1670 and 1700 cm$^{-1}$ and C—N stretch at 1605 cm$^{-1}$.

$^1$H NMR δ 0.8 ($CH_3$ of hexyl group, 3H, t) 1.3 ($CH_3$ of $CO_2CH_2CH_3$ plus $CH_2$ of hexyl chain, 11H, m) 2.6 ($CH_2$—CO, 2H t), 3.6 ($CH_2$—N, 2H, t), 4.1 ($CH_2$—O of hexyl group, 2H t), 4.3 ($CH_2$ of ester, 2H m), 6.5 (aromatic C—H, 2H m), 7.85 (aromatic C—H 2H m).

This Example demonstrates that the reaction of acrylates with primary aromatic amines yields predominantly mono-adducts.

Example 13

Reaction of pentaerythritol tetra acrylate with N-methylaniline

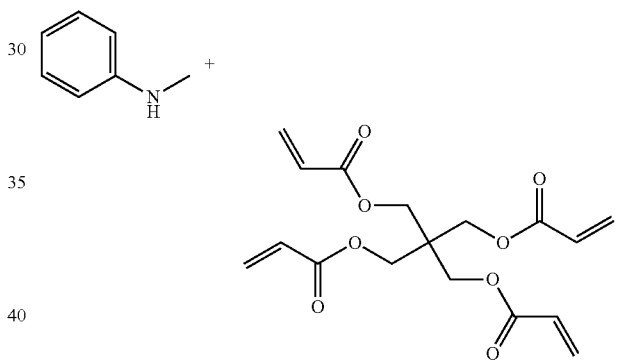

Synthesis of tetra-(hydroxymethyl)methane tetra-(3-[N-methyl-N-phenylamino]propionate)

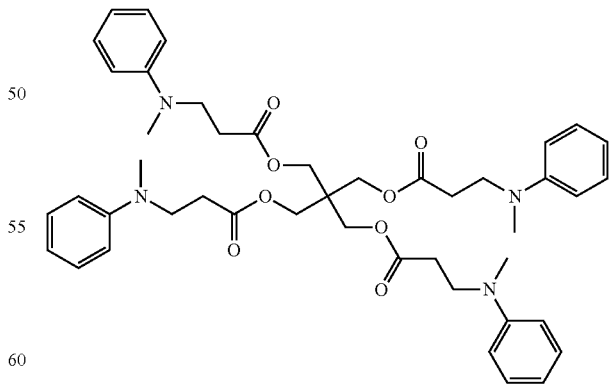

Pentaerythritol tetraacrylate (4.4 g, 0.0125 moles) was added to N-methylaniline (5.4 g 0.050 moles), dissolved in glacial acetic acid (10 ml). The mixture was heated with stirring at 100° C. for 2 hours and then the acetic acid removed by vacuum distillation. An infrared spectrum of the residual oil revealed the presence of a little unreacted N-methylaniline but little sign of any unreacted acrylate groups. Absorptions due to the presence of a saturated ester (1730 cm$^{-1}$) and an aromatic amine (1600 cm$^-$) were found. $^1$H NMR δ 2.6 (CH$_2$—CO, 8H t), 2.9 (CH$_3$—N 12H s) 3.6 (CH$_2$—N, 8H, t), 4.1 (CH$_2$—O 8H s), 6.7 (aromatic protons 12H) 7.2 (aromatic protons 8H).

This Example illustrates the reaction with a tetrafunctional acrylate. Higher functionality acrylates can achieve higher amine content, but more extreme reaction conditions may be required.

Example 14

Reaction of di-trimethylolpropane tetracrylate with N-methylaniline

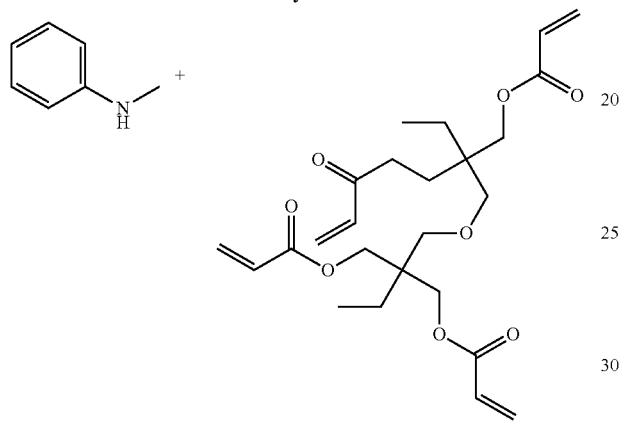

Synthesis of 2,2'-oxybis(methylene)bis(2-ethyl-1,3-propanediol)tetra-(3-[N-methyl-N-phenylamino] propionate)

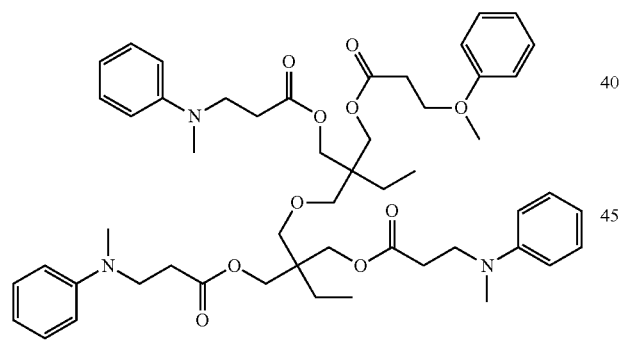

N-methylaniline (7.0 g 0.065 moles) was added to ditrimethylolpropane tetracrylate (4.5 g 0.01 moles) in glacial acetic acid (15 ml). The mixture was heated at 100° C. for 2 hours. The glacial acetic acid was removed by vacuum distillation and the residue submitted to steam distillation to remove the unreacted N-methylaniline. The residue from the steam distillation was extracted with toluene (30 ml). The toluene layer was washed twice with water (40 ml) and then dried over anhydrous magnesium sulphate. Following filtration to remove the magnesium sulphate, the toluene was removed by vacuum distillation to leave a light-brown coloured oil (7.1 g). An infra red spectrum showed that the acrylate had been totally consumed during reaction and that the steam distillation had been effective in removing unreacted methylaniline.

An infrared spectrum of the residual oil showed strong absorptions due to the ester group (1730 cm$^{-1}$) and aromatic amine (1600 cm$^{-1}$). $^1$H NMR δ 0.84 (CH$_3$ of C$_2$H$_5$ 6H t), 1.4 (CH$_2$ 4H q), 2.55 (CH$_2$—CO, 8H t), 2.9 (CH$_3$—N, 12H s), 3.2 (CH$_2$—O, 4H s), 3.6 (CH$_2$—N, 8H, t), 4.0 (CH$_2$—O, 8H, s), 6.7 (aromatic C—H 12H m), 7.2 (aromatic C—H, 8H m).

The following Examples 15, 16, and 17, like Example 10, demonstrate reactions of multifunctional second generation acrylates.

Example 15

Reaction of propoxylated glycerol triacrylate with N-methylaniline

Synthesis of propane-1,2,3-triol tri-(3-[N-methyl-N-phenylamino]propionate)

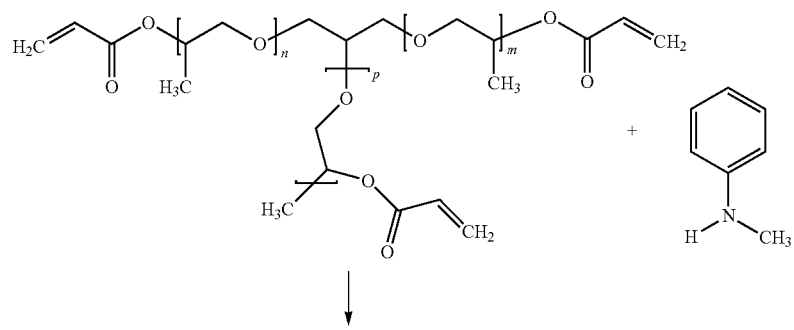

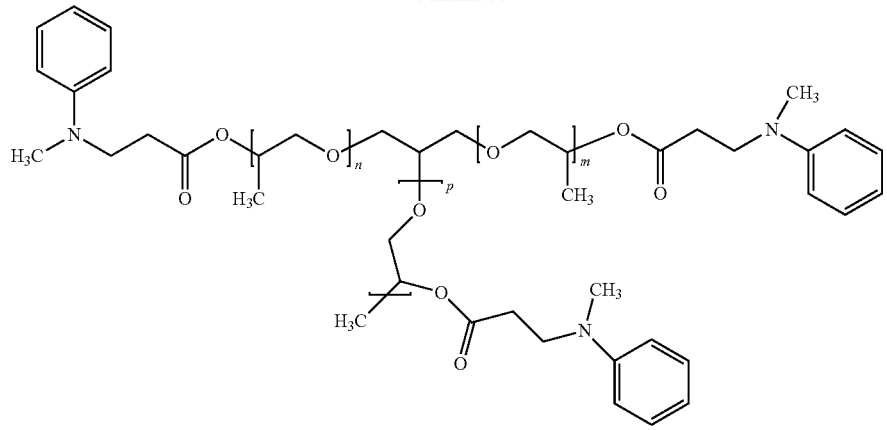

Propoxylated glycerol triacrylate (GPTA—OTA 480, 5.08 g) was added to N-methylaniline (6.42 g—an equivalent amount required to react with the three acrylate groups, had the reactant been glycerol triacrylate) in glacial acetic acid (10 ml). The reaction mixture was heated at 100° C. for 2 hours and then the acetic acid removed by vacuum distillation. A portion of the residue (11 g) was then subjected to steam distillation to remove the excess N-methylaniline and the product extracted with dichloromethane (25 ml). The extract was dried over anhydrous magnesium sulphate, filtered and the dichloromethane removed by distillation in vacuo to leave a pale brown-coloured oil (6.46 g).

IR (thin film), 1730 cm$^{-1}$ (ester carbonyl), 1600 cm$^{-1}$ (C—N stretch).

$^1$H NMR δ (ppm) 1.1 (CH$_3$ of propoxy groups), 2.6 (CH$_2$—CO, t), 2.9 (CH$_3$—N s) 3.5 (CH$_2$—O of propoxy group) 3.65 (CH$_2$—N, t), 6.7 (aromatic protons) 7.2 (aromatic protons).

Example 16

Reaction of ethoxylated trimethylolpropane triacrylate (Cytec Irr 560) with N-methylaniline

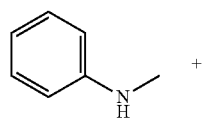

Synthesis of ethoxylated 1,1,1-trimethylolpropane tri-(3-[N-methyl-N-phenylamino]propionate)

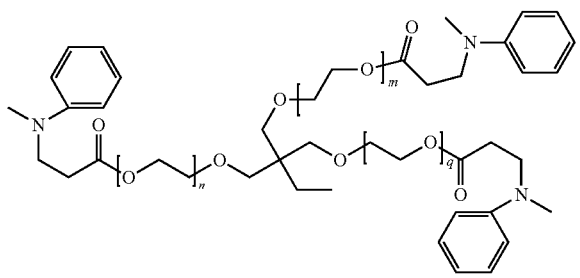

The triacrylate (7.4 g) was added to N-methylaniline (8.025 g—an amount needed to react with three acrylate groups, if the reactant had been trimethylolpropane triacrylate) in glacial acetic acid (10 ml). The reaction mixture was heated at 100° C., with stirring, for 2 hours and then the acetic acid removed by vacuum distillation. A portion of the residue (6.04 g) was subjected to steam distillation to remove the excess N-methylaniline and the product extracted with dichloromethane (25 ml). The extract was dried over anhydrous magnesium sulphate, filtered and the dichloromethane removed by distillation in vacuo to leave a pale brown-coloured oil (3.35 g).

IR (thin film), 1730 cm$^{-1}$ (ester carbonyl), 1600 cm$^{-1}$ (C—N stretch).

$^1$H NMR δ (ppm) 0.8 (CH$_3$, t), 1.4 (CH$_2$, q) 2.6 (CH$_2$—CO m) 2.9 (CH$_3$—N s) 3.4 to 3.8 (CH$_2$—N plus CH$_2$—O of poly ether m), 4.0 (CH$_2$—O, methylol m) 6.7 (aromatic protons) 7.2 (aromatic protons).

Example 17

Reaction of Ethoxylated pentaerythritol tetraacrylate (Sartomer SR494) with N-methylaniline

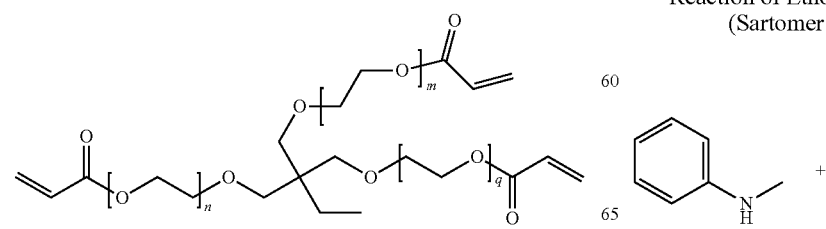

-continued

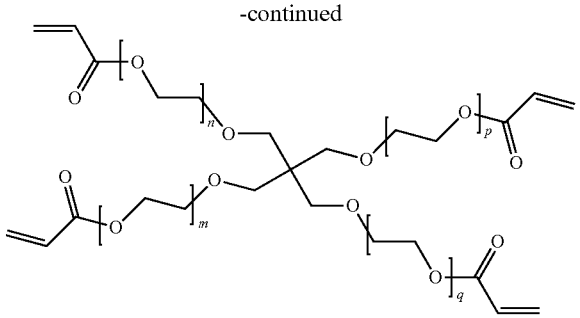

Synthesis of ethoxylated
tetra-(hydroxymethyl)methane
tetra-(3-[N-methyl-N-phenylamino]propionate)

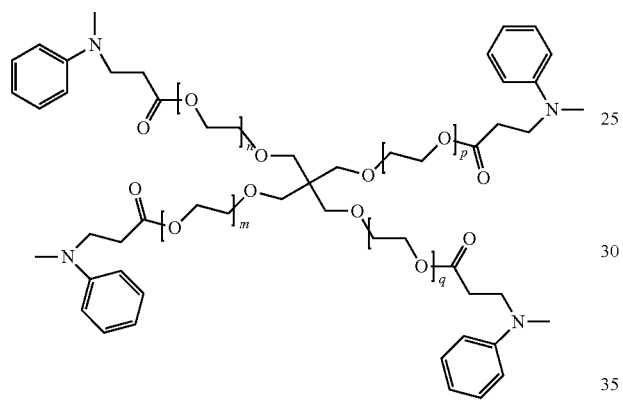

The ethoxylated tetraacrylate (4.45 g) was added to N-methylaniline (5.4 g—sufficient to react with four acrylate groups, if the reactant had been pentaerythritol tetra acrylate) in glacial acetic acid (10 ml). The reaction mixture was heated at 100° C., with stirring, for 2 hours and then the acetic acid removed by vacuum distillation. A portion of the residue (8.95 g) was subjected to steam distillation to remove the excess N-methylaniline and the product extracted with toluene (25 ml). The extract was dried over anhydrous magnesium sulphate, filtered and the toluene removed by distillation in vacuo to leave a pale brown-coloured oil (5.15 g).

IR (thin film), 1730 cm$^{-1}$ (ester carbonyl), 1600 cm$^{-1}$ (C—N stretch).

$^1$H NMR δ (ppm) 2.6 ($CH_2$—CO m) 2.9 ($CH_3$—N s), 3.4 to 3.8 ($CH_2$—N plus $CH_2$—O of poly ether m), 4.0 ($CH_2$—O, methylol m) 6.7 (aromatic protons) 7.2 (aromatic protons).

Materials

Example 18

Reaction of poly(ethylene glycol) diacrylate with N-methylaniline

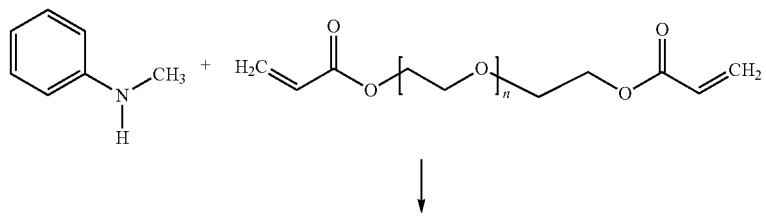

↓

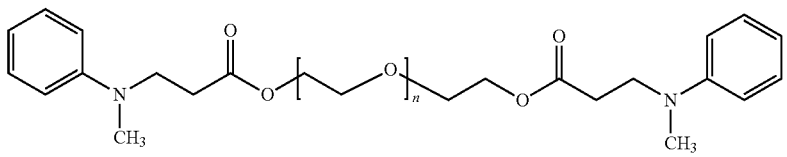

Where n ~ 2

N-methylaniline (6.50 g) was added to poly(ethylene glycol) diacrylate (6.00 g, $M_n \sim 258$) in glacial acetic acid (15 ml). The mixture was heated at 100° C. for 5.5 hours. The glacial acetic acid was removed by vacuum distillation and the residue subjected to steam distillation to remove unreacted N-methylaniline. The residue from the steam distillation was extracted with toluene (75 ml). The toluene layer was washed with water (2×35 ml) and then dried over anhydrous magnesium sulphate. The drying agent was removed by filtration and the toluene removed by vacuum distillation to give a brown-coloured oil (9.86 g). The product showed strong absorptions in its IR spectrum due to the ester group (1735 cm$^{-1}$) and aromatic amine (1600 cm$^{-1}$).

Example 19

Reaction of trimethylolpropane triacrylate with a deficit N-methylaniline to give an amino acrylate

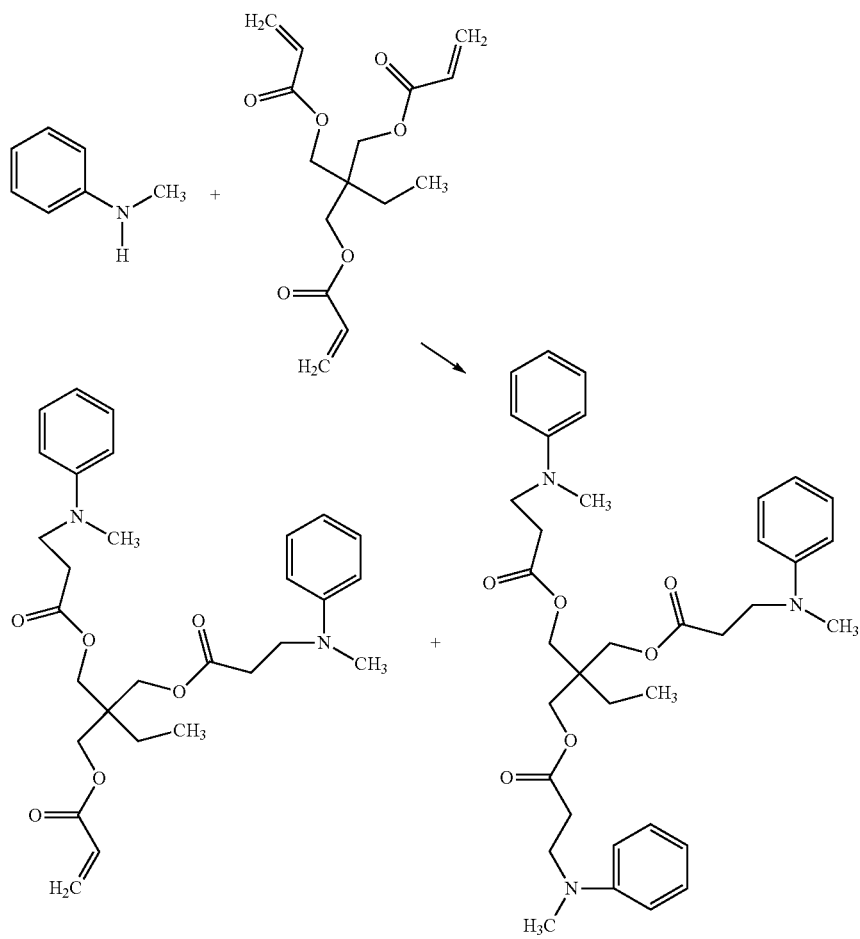

N-methylaniline (9.63 g, 0.09 moles) was added to trimethylolpropane triacrylate (14.81 g, 0.05 moles) in glacial acetic acid (15 ml). The mixture was heated at 100° C. for 8.0 hours. The glacial acetic acid was removed by vacuum distillation. The residue (20.5 g,) showed strong absorptions in its IR spectrum due to the ester group (1670 cm$^{-1}$) and aromatic amine (1700 cm$^{-1}$) as well as signals due to acrylate residues (810 cm$^{-1}$). This product was used as an acrylated amine, and can serve as a polymerisable amine synergist.

Example 20

Reaction of N,N-dimethylacrylamide with N-methylaniline

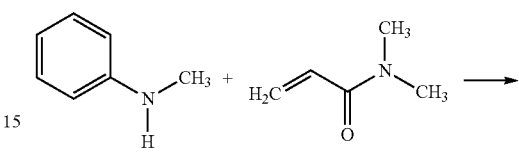

-continued

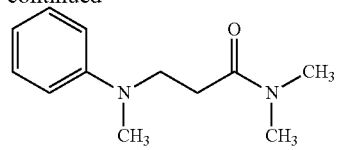

N-methylaniline (5.35 g, 0.05 moles) was added to N,N-dimethylacrylamide (6.45 g, 0.05 moles) in glacial acetic acid (10 ml). The mixture was heated at 100° C. for 12.0 hours. The glacial acetic acid was removed by vacuum distillation. The residue (11.7 g,) showed strong absorptions in its IR spectrum due to the amide groups (1640 cm$^{-1}$) and aromatic amine (1600 cm$^{-1}$). $^1$H NMR δ 2.55 (CH$_2$—CO, 2H t), 2.9-3.0 (CH$_3$—N 9H m), 3.65 (CH$_2$—N), 4.1 6.7 (aromatic C—H 3H m), 7.2 (aromatic C—H, 2H m).

This Example illustrates the use of alternative Michael acceptors of the invention. Acrylamides are useful in the dental industry, for example.

Example 21

Reaction of acrylic acid with N-methylaniline

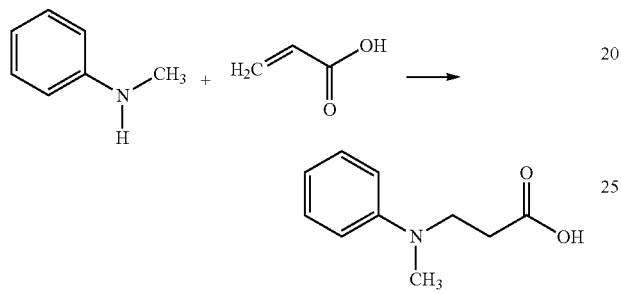

N-methylaniline (10.7 g, 0.1 mole) was added to acrylic acid (7.0 g, 0.97 moles) in glacial acetic acid (15 ml). The mixture was heated at 100° C. for 12.0 hours. The glacial acetic acid was removed by vacuum distillation. The residue (17.0 g) showed absorptions in its IR spectrum associated with a carboxyl group (1720 cm$^{-1}$) and aromatic amine (1600 cm$^{-1}$). $^1$H NMR δ 2.55 (CH$_2$—CO, 2H t), 2.9-3.0 (CH$_3$—N 3H s), 3.65 (CH$_2$—N), 4.1 6.7 (aromatic C—H 3H m), 7.2 (aromatic C—H, 2H m) 10.8 (CO$_2$H 1H s).

This Example demonstrates that an amine can be added to acrylic acid. Addition to methacrylic acid is also possible. The resulting products may be further elaborated to generate multifunctional amine synergists by reaction with polyols, and are especially useful where acrylates of the polyol are not available.

Example 22

Reaction of ethyl 4-aminobenzoate with trimethylolpropane triacrylate

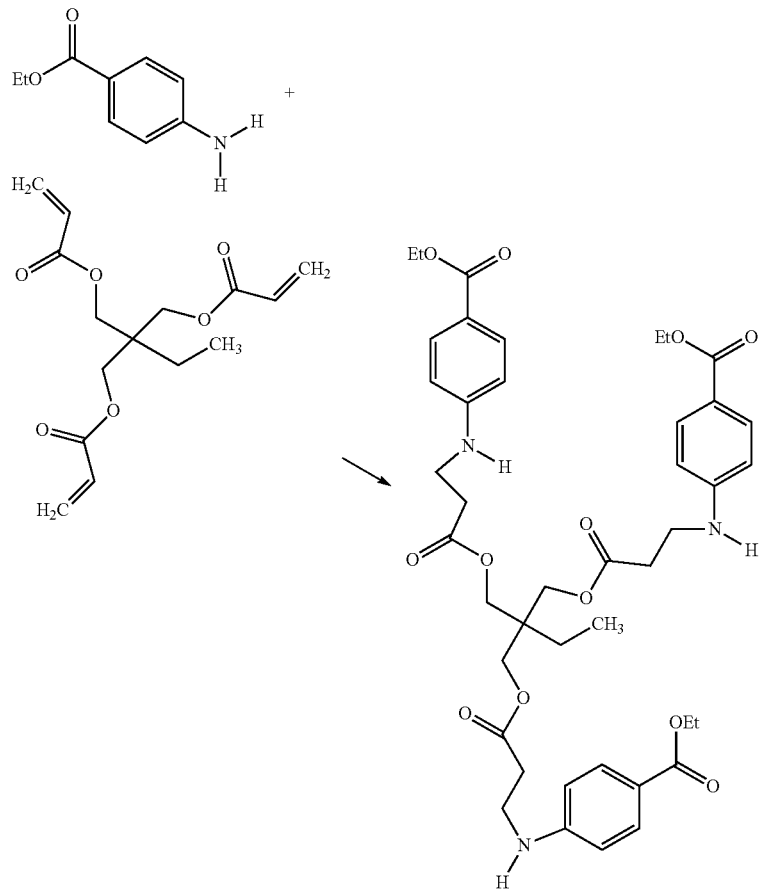

Ethyl 4-aminobenzoate (3.5 g, 0.021 moles) was added to trimethylolpropane triacrylate (9.9 g 0.033 moles) in glacial acetic acid (15 ml). The mixture was stirred and heated at 100° C. for 14 hours followed by removal of the acetic acid by distillation in vacuo. The residue showed strong absorptions in its IR spectrum due to a secondary N—H group at 3390 cm$^{-1}$ plus acrylate groups at 810 cm$^{-1}$.

Methylation of the Product Produced by Reacting Ethyl 4-Aminobenzoate with Trimethylolpropane Triacrylate

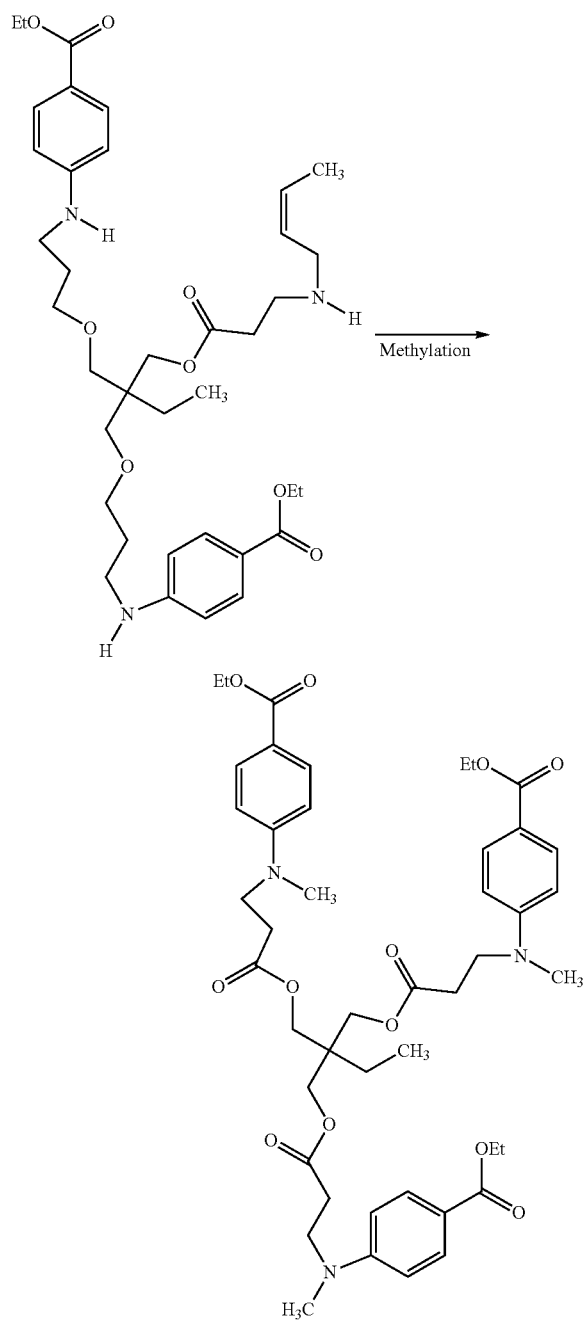

Methylation of the secondary amine was carried out according to the procedure of Borch and Hassid (R F Borch and A I Hassid Journal of Organic Chemistry 1972, 37(10) 1673-1674). The secondary amine (3 g) was dissolved in acetonitrile (8 ml). To this stirred solution was added aqueous formaldehyde (4 ml, 37% aqueous solution), followed by sodium cyanoborohydride (1 g). After 2 hours, glacial acetic acid (0.5 ml) was added, and stirring continued for a further 2 hours. The acetonitrile was removed by distillation in vacuo and the residue taken up in dichloromethane (20 ml). The dichloromethane solution was washed with water (2×20 ml) and dried over anhydrous magnesium sulfate. Removal of the drying agent by filtration and the dichloromethane by distillation in vacuo left a residue (2.9 g), an IR spectrum of which showed that ~65% methylation had occurred. This residue was methylated using formaldehyde (4 ml) and sodium cyanoborohydride (1 g), by the previously described procedure, to give a residue of 2.5 g. An IR spectrum of the residue showed an absorption due to the C—N stretch of the aromatic amine at 1600 cm$^{-1}$ and absorptions at 1695 and 1735 cm$^{-1}$ due an aromatic/unsaturated ester and a saturated ester group respectively. An absorption at 810 cm$^{-1}$cm is characteristic of the presence of acrylate groups.

An alternative method of methylation of the secondary amine-adduct formed between ethyl 4-aminobenzoate and trimethylolpropane triacrylate was also explored. To the adduct (9.15 g, 0.0116 mole), ethyl di-isopropylamine (2 g) was added dropwise followed by dimethyl sulfate 1.5 g, 0.0119 mole. As the mixture was heated up to 120° C. the solution became homogeneous. After keeping the mixture at 120° C. for 4 hours the solution was allowed and then poured into a mixture of water (80 ml) and dichloromethane (20 ml). After 20 mins. stirring, the dichloromethane layer was separated from the water and washed with water (2×25 ml water). Following drying of the dichloromethane layer with anhydrous magnesium sulfate, the solvent was removed by distillation in vacuo to leave a residue (5.1 g). An IR spectrum showed that some secondary amide was present. The residue was reacted as before using ethyl di-isopropylamine (2.5 g) and dimethyl sulfate (1.5 g). Work up left a residue of 4.2 g, an IR spectrum of which showed that full methylation had been achieved.

This Example provides a substituted amine synergist.

Example 23

Reaction of N-ethylaniline with trimethylolpropane triacrylate

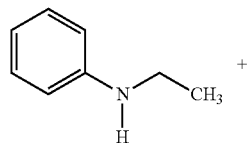

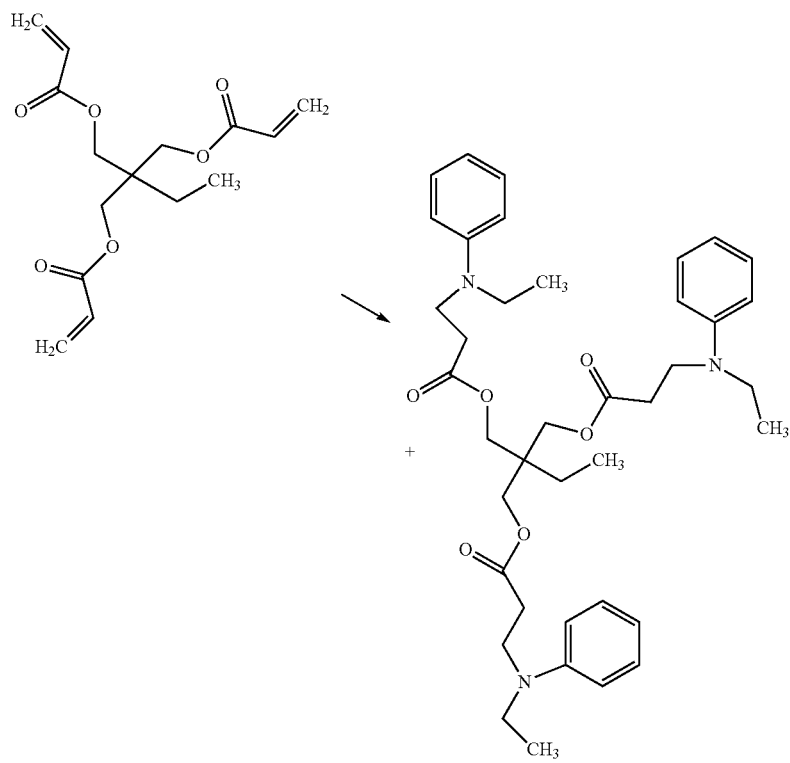

N-Ethylaniline (10 g, 0.083 moles) was added to trimethylolpropane triacrylate (7.4 g, 0.025 moles) in glacial acetic acid (10 ml) and the mixture heated with stirring at 100° C. for 5 hours. The acetic acid was removed by distillation in vacuo to give a residue which contained N-ethylaniline. The latter was removed by steam distillation to give a brown-coloured oil (14.4 g) which showed in its IR spectrum absorptions due to the ester group (1725 $cm^{-1}$) and a C—N stretch of an aromatic amine (1600 $cm^{-1}$).

$^1$H NMR δ 0.9 ($CH_3$, 3H, t), 1.15 ($CH_3$—$CH_2$—N, 9H t), 1.4 ($CH_2$, 2H, q), 2.5 ($CH_2$—CO, 6H t), 3.4 ($CH_3$—$CH_2$—N, 6H, q), 2.9 ($CH_3$—N, 9H s), 3.6 ($CH_2$—N, 6H, t), 4.0 ($CH_2$—O, 61-1, s), 6.7 (aromatic C—H 9H m), 7.2 (aromatic C—H, 6H m).

This Example makes use of N-ethyl aniline as the amine. Subsequent tests (infra) show that the N-methyl compounds tend to be preferable, although the n-ethyl compounds may be preferred under certain circumstances.

Example 24

Reaction of N-methylaniline with di-pentaerythritol hexa-acrylate

This Example demonstrates the formation of a hexafunctional material.

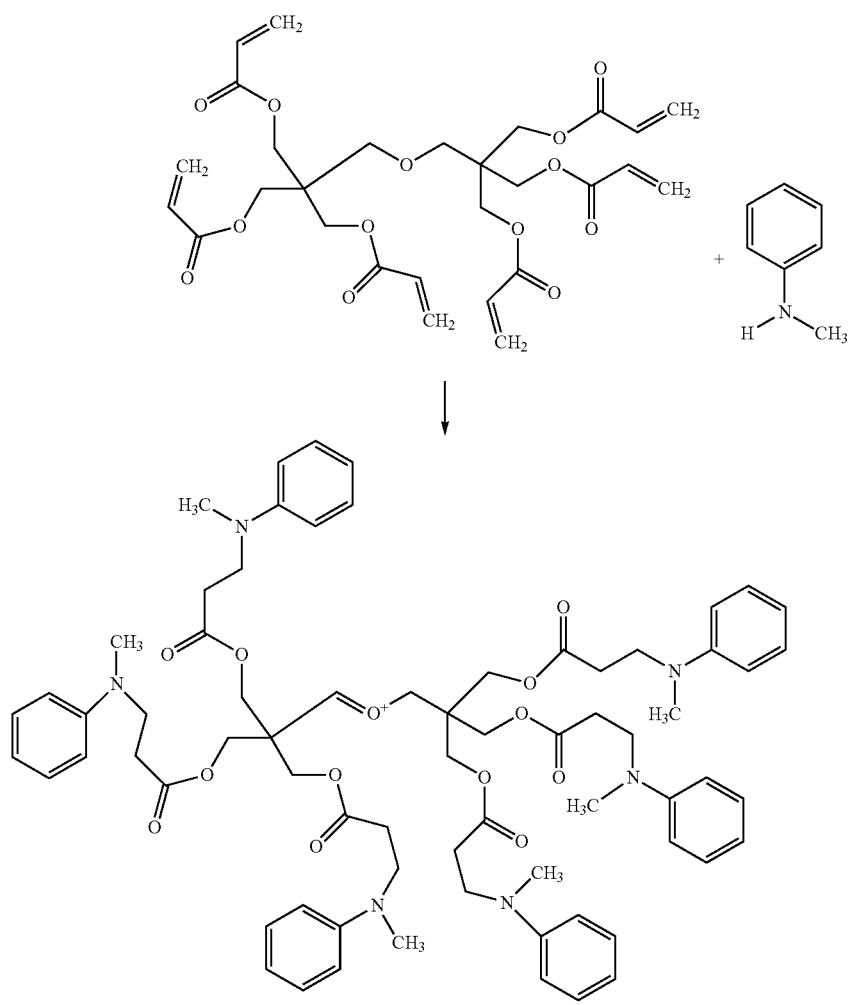

N-methylaniline (7.5 g, 0.07 moles) was added to di-pentaerythritol hexa-acrylate (6.74 g, 0.01 moles) in glacial acetic acid (15 ml). The mixture was stirred and heated at 100° C. for 5.5 hours. The acetic acid was removed by distillation in vacuo to give a residue which contained N-methylaniline. The latter was removed by steam distillation to give a brown-coloured oil 7.3 g, which showed in its IR spectrum absorptions, due to the ester group (1735 cm$^{-1}$) and a C—N stretch of an aromatic amine (1600 cm$^{-1}$).

Example 25

Reaction of an acrylated benzophenone with N-methylaniline to create a photoinitiator containing an aromatic amine synergist The acrylated benzophenone (6.0 g) was added to N-methylaniline (6.5 g) dissolved in glacial acetic acid (10 ml) and the mixture heated, with stirring, at 100° C. for 7 hours. The glacial acetic acid was removed by distillation in vacuo. The residue was subjected to steam distillation to remove the excess N-methylaniline. Extraction of the steam-involatile component with dichloromethane (50 ml) gave, after drying and removal of the solvent, a slightly blue-coloured oil (6.36 g). An IR spectrum of the oil showed absorptions at 1720 cm$^{-1}$ (aliphatic ester), 1670 cm$^{-1}$ (aromatic ketone) and 1600 cm$^{-1}$ (C—N stretch of an aromatic amine). $^1$H NMR, δ 2.6 CH$_2$—CO m) 2.95 (CH$_3$—N, s), 3.6-3.8, CH$_2$—N plus CH$_2$—O m), 6.7 to 7.8 (aromatic C—H).

This Example demonstrates that a photoinitiator, in this case benzophenone, may be incorporated into an aromatic amine synergist.

The following Examples 26-36 demonstrate how an aliphatic amine may be introduced into an aromatic amine synergist. The subsequent Examples show how this improves cure rate.

Example 26

Michael addition of a deficit of N-methylaniline (75% of the theoretical amount) to trimethylolpropane triacrylate with a further addition of 2-N-methylaminoethanol N-Methylaniline (12.04 g, 0.1125 moles) was added to glacial acetic acid (15 ml) containing trimethylolpropane triacrylate (14.81 g, 0.05 moles) and the mixture heated, with stirring, at 100° C. for 12 hours. The glacial acetic acid was removed by distillation in vacuo. An IR spectrum of the residue showed the presence of some unreacted acrylate groups. 2-N-methylaminoethanol (2.82 g, 0.0375 moles) was added to the residue and the mixture heated at 100° C. for 2.5 hours, by which time the solution was homogeneous. An IR spectrum of the cooled reaction product (29 g) showed that all the acrylate groups had been consumed in the reaction, as had all the secondary aliphatic amine groups, and absorptions were present indicating the presence of an aliphatic ester (1730 cm$^{-1}$) and an aromatic amine (1600 cm$^{-1}$). $^1$H NMR, δ 0.8 (CH$_3$ of ethyl group, m) 1.4 (CH$_2$— of ethyl group, m), 2.3 (CH$_3$ of ethanolamine, s), 2.6 (CH$_2$—C) and CH$_2$ of ethanolamine, m), 2.95 (CH$_3$—N), 3.6 (CH$_2$—N of aminoacrylate m), 4.0 (CH$_2$—O, t), 6.7 (C—H of aromatic), 7.2 (C—H of aromatic).

Example 27

Michael addition of a deficit of N-methylaniline (60% of the theoretical amount) to trimethylolpropane triacrylate with a further addition of 2-N-methylaminoethanol The procedure described in Example 24 was followed using trimethylolpropane triacrylate (14.81 g, 0.05 moles), N-methylaniline (9.63 g, 0.09 moles), 2-N-methylaminoethanol (4.5 g, 0.06 moles) and glacial acetic acid (15 ml). An IR spectrum of the cooled reaction product (28 g) showed that all the acrylate groups had been consumed in the reaction, as had all of the secondary aliphatic amine.

Example 28

Michael addition of a deficit of N-methylaniline (85% of the theoretical amount) to trimethylolpropane triacrylate with a further addition of 2-N-methylaminoethanol The procedure described in Example 24 was followed using trimethylolpropane triacrylate (14.81 g, 0.05 moles), N-methylaniline (13.80 g, 0.1275 moles), 2-N-methylaminoethanol (1.69 g, 0.0225 moles) and glacial acetic acid (15 ml). An IR spectrum of the cooled reaction product (28 g) showed that all the acrylate groups had been consumed in the reaction, as had all the secondary aliphatic amine.

Example 29

Michael addition of a deficit of N-methylaniline (75% of the theoretical amount) to di-trimethylolpropane tetra-acrylate with a further addition of 2-N-methylaminoethanol The procedure described in Example 24 was followed using di-trimethylolpropane tetra-acrylate (15.00 g, 0.033 moles), N-methylaniline (10.7 g, 0.10 moles), 2-N-methylaminoethanol (2.40 g, 0.032 moles) and glacial acetic acid (15 ml). An IR spectrum of the cooled reaction product (27 g) showed that all the acrylate groups had been consumed in the reaction, as had all the secondary aliphatic amine.

Example 30

Michael addition of a deficit of N-methylaniline (60% of the theoretical amount) to di-trimethylolpropane tetra-acrylate with a further addition of 2-N-methylaminoethanol The procedure described in Example 27 was followed using di-trimethylolpropane tetra-acrylate (15.00 g, 0.033 moles), N-methylaniline (9.64 g, 0.09 moles), 2-N-methylaminoethanol (3.32 g, 0.042 moles) and glacial acetic acid (15 ml). An IR spectrum of the cooled reaction product (29 g) showed that all the acrylate groups had been consumed in the reaction, as had all the secondary aliphatic amine.

Example 31

Michael addition of a deficit of N-methylaniline (75% of the theoretical amount) to di-trimethylolpropane tetra-acrylate with a further addition of morpholine The procedure described in Example 27 was followed using di-trimethylolpropane tetra-acrylate (15.00 g, 0.033 moles), N-methylaniline (10.7 g, 0.10 moles), morpholine (2.78 g, 0.132 moles) and glacial acetic acid (15 ml). An IR spectrum of the cooled reaction product (28 g) showed that all the acrylate groups had been consumed in the reaction, as had all the secondary aliphatic amine.

Example 32

Michael addition of a deficit of N-methylaniline (60% of the theoretical amount) to di-trimethylolpropane tetra-acrylate with a further addition of morpholine The procedure described in Example 27 was followed using di-trimethylolpropane tetra-acrylate (15.00 g, 0.033 moles), N-methylaniline (9.64 g, 0.09 moles), morpholine (3.65 g, 0.042 moles) and glacial acetic acid (15 ml). An IR spectrum of the cooled reaction product (26 g) showed that all the acrylate groups had been consumed in the reaction, as had all the secondary aliphatic amine.

Example 33

Michael addition of a deficit of N-methylaniline (75% of the theoretical amount) to penta-erythritol tetra-acrylate with a further addition of 2-N-methylaminoethanol The procedure described in Example 27 was followed using penta erythritol tetra-acrylate (3.52 g, 0.01 moles), N-methylaniline (3.21 g, 0.030 moles), 2-N-methylaminoethanol (0.75 g, 0.010 moles) and glacial acetic acid (15 ml). An IR spectrum of the cooled reaction product (5.2 g) showed that all the acrylate groups had been consumed in the reaction, as had all the secondary aliphatic amine.

Example 34

Michael addition of a deficit of N-methylaniline (60% of the theoretical amount) to penta-erythritol tetra-acrylate with a further addition of 2-N-methylaminoethanol The procedure described in Example 27 was followed using penta erythritol tetra-acrylate (3.52 g, 0.01 moles), N-methylaniline (2.57 g, 0.024 moles), 2-N-methylaminoethanol (1.20 g, 0.016 moles) and glacial acetic acid (15 ml). An IR spectrum of the cooled reaction product (4.70 g reaction, as had all the secondary aliphatic amine.) showed that all the acrylate groups had been consumed in the reaction, as had all the secondary aliphatic amine.

Example 35

Michael addition of a deficit of N-methylaniline (75% of the theoretical amount) to tripropylene glycol diacrylate with a further addition of 2-N-methylaminoethanol The procedure described in Example 24 was followed using tripropylene glycol diacrylate (6.0 g, 0.02 moles), N-methylaniline (3.21 g, 0.03 moles), 2-N-methylaminoethanol (0.75 g, 0.01 moles) and glacial acetic acid (10 ml). An IR spectrum of the cooled reaction product (9.1 g) showed that all the acrylate groups had been consumed in the reaction, as had all the secondary aliphatic amine.

Example 36

Michael addition of a deficit of N-ethylaniline (75% of the theoretical amount) to trimethylolpropane triacrylate with a further addition of 2-N-methylaminoethanol.

The procedure described in Example 24 was followed using N-ethylaniline (6.05 g, 0.056 moles), trimethylolpropane triacrylate (TMPTA, 7.4 g, 0.025 moles), 2-N-methylaminoethanol (1.42 g, 0.018 moles) and glacial acetic acid (15 ml). An IR spectrum of the cooled reaction product (14.0 g) showed that all the acrylate groups had been consumed in the reaction, as had all the secondary aliphatic amine and absorptions were present which are associated with aliphatic esters (1730 cm$^{-1}$) and the C—N stretch of aromatic amines (1600 cm$^{-1}$) $^1$H NMR δ 0.8 (CH$_3$ of TMPTA, m), 1.2 (CH$_3$ of N-ethyl), 1.5 (CH$_2$ of ethyl group of TMPTA, m) 2.0 (N—CH$_3$ of N-methylamino residue, s), 2.6 (CH$_2$—N from ethanolamine plus CH$_2$—CO m), 3.4 (CH$_2$ of N-ethyl, q), 3.6 (CH$_2$—N of the amino acrylate t), 4.0 (CH$_2$—O q), 6.7 (C—H of aromatic, m), 7.2 (C—H of aromatic).

Example 37

Reaction of N-methylaniline with trimethylolpropane triacrylate using a clay catalyst This reaction was performed in a similar manner to that of Example 4, but wherein the acetic acid catalyst is replaced by a clay catalyst.

The clay catalyst, Montmorillonite Type K10, was activated by heating in air at 100° C. for 24 hours. Trimethylolpropane triacrylate (7.4 g) was added to N-methylaniline (8.025 g) followed by the clay catalyst (0.77 g) and toluene (0.5 ml). The mixture was heated, with stirring and under vacuum, at 100° C. for 20 hrs. The solution became a deep blue in colour. The cooled reaction mixture was dissolved in dichloromethane (35 ml), filtered and the solvent removed in vacuo to leave a blue-coloured oil. An IR spectrum of the oil showed the presence of a little unreacted N-methylaniline (N—H absorption at 3410 cm$^{-1}$), a little unreacted acrylate (810 cm$^{-1}$) and strong absorptions due to a saturated ester (1735 cm$^{-1}$) and aromatic amine (1600 cm$^{-1}$). In all other respects the spectrum closely resembled that of the product produced on Example 4. While a clay catalyst can be used to effect the Michael addition, this Example shows that it is not as efficacious as glacial acetic acid as the catalyst (c.f. Example 4).

Example 38

Reaction of aniline with hexan-1,6-diol diacrylate with a deficit (0.001 moles) of aniline followed by reaction with N-methylaniline Hexan-1,6-diol diacrylate (4.52 g, 0.02 moles) was added to glacial acetic acid (10 ml) containing aniline (0.093 g, 0.001 moles) and the mixture heated with stirring at 100° C. for 6 hours. The acetic acid was removed by distillation in vacuo to give a dark-coloured oil, an IR of which displayed absorptions at 1620 and 1640 cm$^{-1}$ (acrylate groups), a small absorption at 1600 cm$^{-1}$ (aromatic amine). An absorption at 3400 cm$^{-1}$ was not observed, indicating that the primary amino group had reacted with two acrylate groups. The residual oil was taken up in glacial acetic acid (10 ml) and N-methylaniline (4.50 g, excess) added, and the mixture heated with stirring at 100° C. for 6 hours. The acetic acid was removed by distillation in vacuo to give a dark-coloured oil, an IR of which displayed absorptions at 1600 cm$^{-1}$ (aromatic amine) and an absorption at 3400 cm$^{-1}$ due to the presence of excess N-methylaniline. No absorptions due to acrylate groups were discernible. The excess N-methylaniline was removed via steam distillation. The steam in-volatile material was extracted with dichloromethane (40 ml). The extract was washed with water, and dried over anhydrous magnesium sulfate. Removal of the solvent via distillation in vacuo gave a dark-coloured oil (7.49 g). An IR spectrum of this material exhibited absorptions due to an aliphatic ester (1740 cm$^{-1}$), an aromatic amine (1600 cm$^{-1}$) and mono-substituted aromatic rings (700 and 750 cm$^{-1}$).

This Example demonstrates that the compounds of the invention can be prepared as oligomers.

Example 39

Reaction of aniline with hexan-1,6-diol diacrylate with a deficit (0.004 moles) of aniline followed by reaction with N-methylaniline The procedure of Example 38 was followed using hexan-1,6-diol diacrylate (4.52 g, 0.02 moles), aniline (0.372 g, 0.004 moles) and N-methylaniline (4.0 g excess). The product (7.79 g) was a dark-coloured oil having an IR spectrum similar to the material produced in Example 38. $^1$H NMR δ 1.4 (CH$_2$ 4H t), 1.7 (CH$_2$, 4H, t), 2.5 (CH$_2$—CO, t), 2.9 (CH$_3$—N, s), 3.6 (CH$_2$—N, t), 4.0 (CH$_2$—O, s), 6.7 (aromatic C—H m), 7.2 (aromatic C—H, m). The ratio of the integrations for the CH$_2$ groups of the hexan-1,6-diol diacrylate to the CH$_3$—N of the aromatic amine show that after the reaction with aniline, ~66.7% of the acrylate groups remain unreacted, i.e. the reaction with aniline consumed ~33% of the acrylate groups.

This Example, in common with Example 38, also demonstrates that the compounds of the invention can be prepared as oligomers.

Example 40

Evaluation of the Aromatic Aminoacrylates as Synergists

A base formulation containing an aromatic epoxy acrylate resin (Actilane 320 F, 84.10 g), reactive diluent tripropylene glycol diacrylate (84.10 g) and photoinitiator 2-iso-propylthioxanthone (2.52 g) was prepared. Solutions containing the synergist to be tested were prepared by adding the synergist (0.3 g) to the base formulation (10 g). Formulations containing the synergist were applied to unlacquered Leneta opacity charts (The Leneta Company, 15 Whitney Road, Mahwah N.J. 07430 U.S.A.) using K-bars—wired bars (R.K. Print Coat Instrument Ltd). The K-bars selected for use lay down films of ~8μ and 40μ thickness, with the actual coat-weight is dependent upon viscosity. The coated chart papers were cured using a Fusion Systems conveyor (DRS 120) equipped with a 600 watts/inch lamp (H-bulb). The conveyor speed was 58 metres per minute. The number of passes under the lamp that were required to cure ~8 μm thick films of the various formulations to touch are shown in Table 1—Column 2. The number of passes to cure formulations containing 2-ethylhexyl N,N-dimethylaminobenzoate (S1) and N,N-dimethylaniline (S2) were also determined. The solvent (methyl ethyl ketone—MEK) resistance of the ~8 μm thick films that had been given 5 passes under the lamp was also determined. The number of double-rubs to cause break-up of the film so as to reveal the underlying layer were recorded (Table 1 column 3) since these give an indication of the effectiveness of cure (See C. Lowe in Test Methods for UV and EB Curable Systems J Wiley and Sons 1996, ISBN 094 7798 072). The number of passes under the lamp of thick films (~40 μm) to achieve cure to touch and through cure (as evaluated using the thumb-twist test) were also evaluated and the results are shown in Table 2.

TABLE 1

Curing of films of ~8 μm thickness

| Example | No. of passes for full cure | No. of double rubs for MEK to break through the film |
|---|---|---|
| 1 | 6-7 | 60 |
| 4 | 6 | 65 |
| 7 | 6 | 70 |
| 9 | 6-7 | 70 |
| 11 | 7 | 250 |
| 13 | 6-7 | 120 |
| 14 | 8 | 55 |
| 15 | 8 | 55 |
| 16 | 7 | 65 |
| 17 | 6 | 60+ |
| 18 | 5 | 100-130 |
| 23 | 7-8 | 55 |
| 24 | 9 | 35 |
| S1 | 5 | >300 |
| S2 | 3 | 50 |

TABLE 2

Determination of the number of passes under the lamp to achieve cure to touch and through cure

| Sample | Passes for cure to touch | Passes for through cure |
|---|---|---|
| 4 | 5 | 6 |
| 11 | 5 | 6 |
| 13 | 4 | 5 |
| 16 | 6 | 7 |
| S1 | 5 | 6 |
| S2 | 2 | 2+ |

These results show that the multifunctional amine synergists are curing as well as the amine synergists S1 (ethyl dimethylminobenzoate) which is frequently used in UV-curable coatings.

Evaluation of the Amount of Amine Synergist that can be Extracted from Some of the Cured Coatings Shown in Table 1

Cured coatings, selected from Table 1, were subjected to solvent extraction. Samples (1 gm) were cut from cards carrying the cured coatings and immersed in acetonitrile (30 ml) contained in a brown glass stoppered bottle for 7 days. Analysis of the acetonitrile solutions was carried out using a UV-spectrometer (PG Instruments, Type T60). UV spectra of the solutions contained in a 1 cm pathlength cuvette, were recorded and then to each solution 0.5 ml of hydrochloric acid (1:1 mixture of concentrated acid and water) and the spectra recorded. Optical densities at 300 nm for the acidified and non-acidified solutions were recorded. Addition of the acid protonated the aromatic amine rendering it transparent at 300 nm. Thus the change in optical density at 300 nm between the acidified and non-acidified solutions gave the absorption due to the amine. The amount of amine extracted was determined using the Beer-Lambert Law:

$$\epsilon_1 c_1 l_1 / \epsilon_2 c_2 l_2 = OD_1 / OD_2$$

where $\epsilon$=molar extinction coefficient, c=concentration in moles/litre and l=pathlength in cm.

Solutions of the appropriate amine synergists were made up at a known concentration and their optical densities determined at 300 nm. Since $l_1$ and $l_2$ are both equal to 1 and $\epsilon_1$ is equal to $\epsilon_2$ and $c_2$ and $OD_2$ are known from the spectrum of the amine synergist the concentration of the amine in the extract can be determined. In this way the amount of amine extracted from 1 gm of coated card can be determined. Knowing the coatweight of the cured film, enables the percentage of extrated amine to be determined.

TABLE 3

Percentage of extractable amine synergist contained in the cured coatings

| Example | % Extracted |
|---|---|
| 4 | 2 |
| 11 | A |
| 13 | A |
| 17 | A |
| 18 | 1.2 |
| S1 | 5 |
| S2 | 10.5 |

A = below the limits of detection

These results demonstrate that the multifunctional amine synergists give rise to little if any extractable amine in fully cured coatings, whereas the parent amine S2 produces a sizeable amount.

This Example explored the utility of the materials of the present invention in a clear varnish for both thin and thick films. Performance was better in the thicker films (Table 2) than with thinner films (Table 1). In nearly every case the performance in thicker films is as good as the commercially available 2-ethylhexyl N,N-dimethylaminobenzoate (EHA). While N,N-dimethylaniline performed well, it cannot be used commercially, due to its odour and volatility.

In this Example, the performance of the compounds of the invention in an ink was assessed. While the materials had a slightly lower reactivity than EHA, this can be attributed to the percentage of nitrogen being lower than in EHA, with the amino group being responsible for performance. The benefit of the materials of the invention is that they are bound into the coating upon cure, so that very little amine can be extracted following cure (Table 3).

Example 41

Performance Evaluation in Offset Inks

The performance of the materials of the present invention was assessed in a black offset ink formulation as shown below. The black offset ink was prepared using a 3-roll mill and was made as an 85 parts (%) recipe, shown in Table 4.

TABLE 4

| Material | % age |
|---|---|
| Ebecryl 846 | 30.0 |
| Photomer 3016 (epoxy acrylate solution in GPTA) | 24.7 |
| Fluorstab UV1 | 1.5 |
| P92 Dispersant | 1.2 |
| Raven 1060 Black Pigment | 5.0 |
| Special Black 250 Pigment | 12.0 |
| Lumiere Violet Pigment | 1.0 |
| SunFast Blue 15:3 Pigment | 5.0 |
| Micronised Talc IT Extra | 3.0 |
| Aerosil R972 | 0.8 |
| Cab-O-Sil LM150 | 0.4 |
| Polyfluo 540 | 0.4 |
| Total | 85.0 |

A photoinitiator blend was added to the black offset ink as 9% of the overall formulation, comprising:

| | | |
|---|---|---|
| 23.4% | Omnipol 9210 | |
| 44.4% | Omnipol TX | |
| 32.2% | Glycerol propoxylate triacrylate (GPTA) | |

The amine synergists of the present invention have been evaluated at a level of 6% in the ink unless otherwise stated in the cure results table (table 5). Where the level of amine synergist is less than 6%, the formulation has been made up to 100% with GPTA. The amount of black offset ink, amine synergist, photoinitiator blend and GPTA used means all inks are 100 parts formulations.

Three control formulations have been made. The first has been made using 2-ethylhexyl p-dimethylaminobenzoate (EHA) as the amine synergist at a level of 6%, as would be typical in a normal commercial formulation as a control. The second control formulation has no amine synergist. In this second control formulation, the ink was made up to 100 parts using GPTA. The third control formulation was made using N,N-dimethylaniline at a level of 6%.

The inks were printed onto a carton board substrate (Incada Exel coated board from Iggesund) to a density of approximately 1.8-2.0 using an IGT C1 print proofer. These were cured at 70 m/min using a Primarc Maxicure UV rig fitted with a single 300 W/inch medium pressure mercury lamp, operating at half power. The number of passes required to cure was measured by a "set-off cure test" which was performed by visually comparing the extent to which, after each pass, the ink has transferred to a piece of blank substrate under 10 tons pressure for 5 seconds. Decreased ink transfer is an indication of superior cure and hardness. The cure results are shown in Table 5.

TABLE 5

Cure speed of inks containing amine synergist materials

| Amine synergist | No. passes to cure |
|---|---|
| EHA | 3 |
| Example 4 | 3-4 |
| Example 7 | 5 |
| Example 8 | >7 |
| Example 9 | 5-6 |
| Example 10 | 4-5 |
| Example 11 (evaluated at 5%) | 6 |
| Example 13 | 3-4 |
| Example 14 | 5 |
| Example 15 | 4-5 |
| Example 16 | 4 |
| Example 17 | 4 |
| Example 18 | 6 |
| Example 20 | >6 |
| Example 22 | 4 |
| Example 23 | 4-5 |
| Example 24 | 3-4 |
| Example 25 | 5 |
| Example 26 | 4 |
| Example 27 | 3 |
| Example 28 | 3-4 |
| Example 29 | 4 |
| Example 30 | 4 |
| Example 31 | 4 |
| Example 32 | 3-4 |
| Example 33 | 4-5 |
| Example 34 | 4-5 |
| Example 35 | 4-5 |
| Example 36 | 4-5 |
| Example 38 | 4-5 |
| Example 39 | 4 |
| N,N-dimethylaniline | 6 |
| No amine synergist | >10 |

The results in table 1 show that the materials are performing as amine synergists and that some are as good as the standard material EHA.

To determine how the inclusion of an aliphatic amine residue in the synergists affected their hydrophobicity, three inks from Table 1 were examined using a Tack-o-scope.

The Tack-o-scope (manufacturer—Testprint BV) aims at studying the interaction of an ink and a fount when put into contact on a set of rollers. The tack of the ink on a rubber roller is recorded as the fount is put into contact and then removed. Also, a metal plate cylinder with hydrophobic (chrome) and hydrophilic (brass) areas is used to monitor the rapidity with which the hydrophilic areas are cleared after fount is put into contact. In this study the Tack-o-scope has been used to carry out a quick evaluation of how well the ink clears the hydrophilic area of the metal plate cylinder. This test gives an indication of the hydrophilicity/hydrophobicity of the ink. This can therefore be related to the hydrophilicity/hydrophobicity of the amine synergist as this is the only variable between the ink samples tested. The result measured in this test is a visual examination of how quickly the hydrophilic area clears and if the hydrophilic area stays clear.

Three inks have been tested using the Tack-o-scope test. The results are shown in the Table 6. The inks tested are the inks from Example 38 with the corresponding synthesis Example numbers.

TABLE 6

| Amine synergist | Tack-o-scope test result | Comments |
| --- | --- | --- |
| EHA | Hydrophilic area cleared and stays clear | Ink is hydrophobic |
| Example 4 | Hydrophilic area cleared and stays clear | Ink is hydrophobic |
| Example 26 | Hydrophilic area cleared but re-coats a little within 30 seconds | Ink is slightly hydrophilic |

This test indicates that the amine synergist made in example 26 is slightly more hydrophilic than the standard (EHA) and the amine synergist made in Example 4.

The extent of this hydrophilicity will be reflected in the choice of secondary aliphatic amine and the extent to which it is incorporated into the aromatic amine synergist.

The experiments in this Example show that introduction of up to 25% aliphatic amine has little effect upon the hydrophobic properties of the ink. This is of considerable benefit where the materials of the invention are for use in litho inks etc where the formulations come into contact with water before curing.

The invention claimed is:

1. A compound of formula (I)

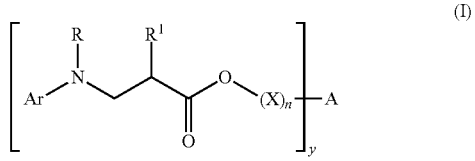

(I)

wherein Ar represents an optionally substituted aryl group, R represents an optionally substituted aryl group, or an optionally substituted straight or branched chain $C_{1-10}$-alkyl group, $R^1$ is H or methyl, X is an extender group, n is 0 or an integer between 1 and 12 inclusive, A is a polyol residue wherein the unsubstituted polyol from which the residue is derived has at least y OH groups, and y is an integer >1, provided that, when R =ethyl, $R^1$ =H, X =polyether chain, and A is a glycerol residue, then Ar is not a 4-carboethoxyphenyl group.

2. A compound according to claim 1, wherein each of Ar or R, when R represents an aryl group, is mono-, bi-, or tricyclic.

3. A compound according to claim 1, wherein each of Ar or R, when R represents an aryl group, is optionally substituted by at least one substituent selected from: OH; AlkOH; Alk; phenyl; alkoxycarbonyl; $H_2NCO(O)$—Alk; HOOC—Alk-; carboxyl; aryl; CO—Alk; arylcarbonyl; —NAlk$_2$; Alk(CO)Ar; Alk(OH)Ar; $CO_2$Alk, and esters thereof; carboxylic acids or a derivative thereof; =O; halogen, including fluorine, chlorine, bromine and iodine; and CN, wherein each Alk is individually alkylene or alkyl and is straight or branched chain having 1 to 10 carbon atoms, preferably having from 1 to 6 carbon atoms, inclusive.

4. A compound according to claim 1, wherein each of Ar or R, when R represents an aryl group, is unsubstituted, or mono-substituted by OH or carboxyl.

5. A compound according to claim 1, wherein any alkyl group contains 1 to 4 carbon atoms.

6. A compound according to claim 1, wherein each of Ar or R, when R represents an aryl group, is individually selected from the group consisting of: phenyl, naphthalene, anthracene, fluorenone, benzophenone, and thioxanthone.

7. A compound according to claim 1, wherein R is substituted methyl or ethyl.

8. A compound according to claim 1, wherein R is alkyl and is substituted by at least one group selected from —CH$_2$COOH and OH.

9. A compound according to claim 1, wherein $R^1$ is H.

10. A compound according to claim 1, wherein X has a formula selected from: —[O(CHR$^2$CHR$^2$ ')$_a$]$_n$—, —[O(CH$_2$)$_b$CO]$_n$—, or —O(CH$_2$)$_b$CO]$_{n-a}$—[O(CHR$^2$CH)]a—, wherein one of $R^2$ and $R^2$ represents a hydrogen atom and the other represents a hydrogen atom, a methyl group, or an ethyl group, n is as defined, a is an integer from 1 to 2, and b is an integer from 4 to 5.

11. A compound according to claim 10, wherein X is selected from; ethyleneoxy, propyleneoxy, caprolactone, and poly(tetrahydrofuran) residues, especially ethoxyl and propoxyl residues.

12. A compound according to claim 10, wherein n is 0 or 1 to 6.

13. A compound according to claim 1, wherein y >1 and <40, or y >1 and <8.

14. A compound according to claim 1, wherein the polyol residue is selected from the group consisting of: tripropylene glycol; pentaerythritol; trimethylolpropane; ditrimethylolpropane; hydroxy terminated polyethers, propylene glycol and butylene glycol; polyesters; polyurethanes; polycarbonates; polycaprolactones; polytetrahydrofurans; and extended versions thereof.

15. A compound according to claim 1, wherein the polyol residue is an acrylated polyol residue selected from the group consisting of; butan-1,4-diol diacrylate, but-2-ene-1,4-diol diacrylate, hexan-1,6-diol diacrylate, triethylene glycol diacrylate, tetraethylene glycol diacrylate, tripropylene glycol diacrylate, tetrapropylene glycol diacrylate, tricyclodecane dimethanol diacrylate, hydroxypivalaldehyde/ trimethylolpropane diacrylate, neopentylglycol diacrylate, ethoxylated neopentyl alcohol diacrylate, propoxylated neopentyl alcohol diacrylate, cyclohexan-l,4-dimethanol diacrylate, propoxylated glyceryl triacrylate, trimethylolpropane triacrylate, ethoxylated trimethylolpropane triacrylate, propoxylated trimethylolpropane triacrylate, caprolactone extended trimethylolpropane triacrylate, pentaerythritol triacrylate, pentaerythritol tetraacrylate, tris-(2-hydroxyethyl) isocyanurate triacrylate, pentaerythritol tri and tetraacrylate, ditrimethylolpropane tetraacrylate, dipentaerythritol penta and hexaacrylate, urethane, epoxy, polyester and polycarbonate acrylates; and extended versions thereof.

16. A compound according to claim 1, as represented by formula (2),

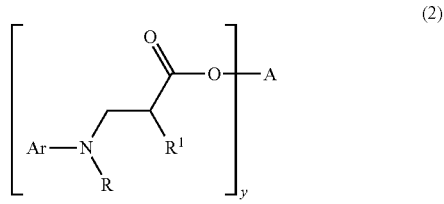

(2)

wherein Ar, A, y, R, and $R^1$ are as defined.

17. A compound according to claim 1, as represented by formula (3)

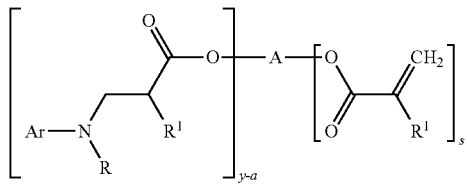

(3)

wherein y-a >2, and wherein Ar, A, y, R, and $R^1$ are as defined.

18. A compound according to claim 1, as represented by formula (4)

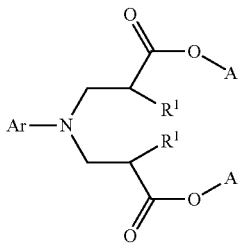

(4)

wherein Ar, A, y, R, and $R^1$ are as defined.

19. The compound of claim 3, wherein the AlkOH is methoxy or ethoxy; the $H_2NCO(O)$—Alk- is urethane; the aryl is phenyl, fluorenone, benzophenone or thioxanthone; the carboxylic acid derivative is an ester or an amide; and the halogen is chlorine or bromine.

20. The compound of claim 14, wherein the polyol residue is ethylene glycol.

* * * * *